United States Patent [19]
Kingston et al.

[11] Patent Number: 6,002,023
[45] Date of Patent: Dec. 14, 1999

[54] 2-DEBENZOYL-2-ACYL TAXOL DERIVATIVES AND METHOD FOR MAKING SAME

[75] Inventors: David G. I. Kingston, Blacksburg, Va.; Ashok Gopal Chaudhary, St. Louis, Mo.; Milind Moreshwar Gharpure, Delhi, India; John Matthew Rimoldi; A.A. Leslie Gunatilaka, both of Blacksburg, Va.

[73] Assignee: Virginia Tech Intellectural Properties, Inc., Blacksburg, Va.

[21] Appl. No.: 08/950,590

[22] Filed: Oct. 15, 1997

Related U.S. Application Data

[60] Division of application No. 08/202,108, Feb. 25, 1994, Pat. No. 5,703,247, which is a continuation-in-part of application No. 08/029,759, Mar. 11, 1993, and a continuation-in-part of application No. 08/030,612, Mar. 11, 1993.

[51] Int. Cl.$^6$ .................................................. C07D 305/14
[52] U.S. Cl. ............................................................ 549/510
[58] Field of Search ............................................. 549/510

[56] References Cited

U.S. PATENT DOCUMENTS

| | | |
|---|---|---|
| 5,015,744 | 5/1991 | Holton et al. . |
| 5,356,928 | 10/1994 | Murray et al. ........................ 599/510 |

FOREIGN PATENT DOCUMENTS

| | | |
|---|---|---|
| WO 93/21173 | 10/1993 | European Pat. Off. . |
| WO 94/08984 | 4/1994 | European Pat. Off. . |

OTHER PUBLICATIONS

Hamada, Nat. Prod Lett. 9(1) p. 47–52, 1996.
Kingston et al., "The Chemistry of Taxol, A Clinically Useful Anti–Cancer Agent", J.Nat. Prod., 53, 1–12 (1990).
Wahl et al., "Rearrangement Reactions of Taxanes: Structural Modifications of 10–Deacetylbaccatin III," Tetrahedron, 48, 6965–6974 (1992).
Farina et al., "The Chemistry of Taxanes: Unexpected Rearrangement of Baccatin III during Chemoselective Debenzoylation with Bu$_3$SnOMe/LiCl," Tetrahedron Lett., 33, 3979–2982 (1992).
Monsarrat et al., "Isolation and Identification of Three Major Metabolites of Taxol and Rat Bile", Drug Metabolism and Disposition, 18, 895–901 (1990).
Py et al., A Novel Rearrangement of the Taxane Skeleton, Bull. Soc. Chim. Fr. 130, 189–191 (1993).
Chen, et al., "Taxol Structure–Activity Relationships: Synthesis and Biological Evaluation of 2–Deoxytaxol," Tetrahedron Lett., 34, 3205–3206 (May 14, 1993).
Klein, "Synthesis of 9–Dihydrotaxol: A Novel Bioactive Taxane," Tetrahedron Lett. 2047–2050 (1993).
Park et al., "New Family of Taxol, Taxotere Analogs Developed," Chem. Eng. News, 36–37 (Apr. 12, 1993).
Swindell et al., "Biologically Active Taxol Analogs With Deleted A–Ring Side–Chain Substituents and Variable C–2' Configurations", J. Med. Chem., 34, 1176–1184 (1991).

Chen et al., "The Chemistry of Taxanes: Reaction of Taxol and Baccatin Derivatives with Lewis Acids in Aprotic and Protic Media," Tetrahedron, 2805–2828 (1993).
Carboni et al., "Synthesis of a Photoaffinity Analog of Taxol as an Approach to Identify the Taxol Binding Site on Microtubules," J. Med. Chem., 36, 513–515 (1993).
Gueritte–Voegelein et al., "Chemical Studies of 10–Deacetyl Baccatin Hemisynthesis of Taxol Derivatives," Tetrahedron, 4451–4460 (1986).
Kingston, "The Chemistry of Taxol", Pharmac. Ther., 52, 1–34 (1991).
Ringel et al., "Studies with RP 56976 (Taxotere): A Semisynthetic Analogue of Taxol", J. Nat. Can., Inst., 4, 288–291 (1991).
Gueritte–Voegelein et al., "Relationships Between the Structure of Taxol Analogues and Their Antimitotic Activity", J. Med. Chem., 34, 992–998 (1991).
Samaranayake et al., Modified Taxols, 8. Deacylation and Reacylation of Baccatin III, J. Nat. Prod., 56, 884–898 (Jun. 1993).
Deutsch et al., "Synthesis of Congeners and Prodrugs 3. Water–Soluble Prodrugs of Taxol With Potent Antitumor Activity", J. Med. Chem., 32, 788–792 (1989).

(List continued on next page.)

*Primary Examiner*—Robert Gersti
*Attorney, Agent, or Firm*—Burns, Doane, Swecker & Mathis, L.L.P.

[57] ABSTRACT

The present invention relates to 2-debenzoyl-2-acyl taxol derivatives, analogues thereof and methods for making same.

Compounds of the present invention include compounds having the general formula:

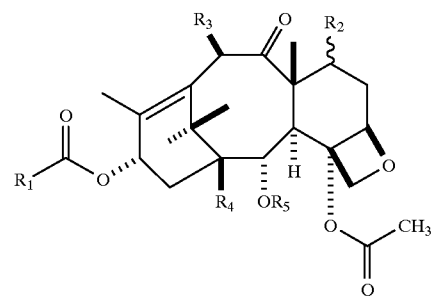

wherein $R_1$ is an alkyl or substituted alkyl; $R_2$ is selected from the group consisting of H and C(O)$R_a$; $R_3$ is selected from the group consisting of H, protecting groups, $R_b$, and C(O)$R_b$; $R_4$ is selected from the group consisting of H and C(O)$R_c$, and wherein $R_a$, $R_b$, and $R_c$ are independently selected from the group consisting of alkyls, substituted alkyls, alkenyls, alkynyls, aryls, and substituted aryls; provided that $R_a$ is other than phenyl and 3-hydroxyphenyl.

1 Claim, 6 Drawing Sheets

OTHER PUBLICATIONS

Mangatal et al., "Application of the Vicinal Oxyamination Reaction with Asymmetric Induction to the Hemisynthesis of Taxol and Analogues", Tetrahedron, 45, 7177–4190 (1989).

Denis et al., "A Highly Efficient,, Practical Approach to Natural Taxol", J. Am. Chem. Soc., 110, 5917–5919 (1988).

Magri et al., J. Org. Chem., 51, 30–39, (1986).

Mathew et al., "Synthesis and Evaluation of Some Water–Soluble Prodrugs and Derivatives of Taxol with Antitumor Activity", J. Med. Chem., 35, 145–151 (1992).

Kingston, et al., "The Taxane Diterpeniods," in Progress in the Chemistry of Organic Natural Products, 61, 1–206, Springer–Verlag (1993).

Appendino, "Taxol (paclitaxel): Historical and Ecological Aspects", Fitoterapia, 6451, 5–25 (1993).

McGuire et al., Taxol: A Unique Antineoplastic Agent with Significant Activity in Advanced Ovarian Epithelial Neoplasms, Ann. Int. Med., 111, 273–279 (1989).

Appendino et al., "Taxoids from the Needles of Yew", Fitoterapia, 6451, 37–46 (1993).

Rowinsky et al., "Taxol: Twenty Years Later, the Story Unfolds," J. Nat. Can. Inst., 1778–1781 (1991).

Holmes et al., "Phase II Trial of Taxol, an Active Drug in the Treatment of Metastic Breast Cancer", J. Nat. Can. Inst., 24, 1791–1805 (1991).

Chaudhary et al., "Modified Taxols. 10. Preparation of 7–Deoxytaxol, a Highly Bioactive Taxol Derivative, and Interconversation of Taxol and 7–epi–Taxol," J. Org. Chem. 58, 3798–3799 (1993).

Georg et al., "Novel Biologically Active Taxol Analogues: Baccatin III 13–(N–(p–Chlorobenzoyl)–2'R, 3'S)–3'–phenylisoserinate) and Baccatin III 13–(N–Benzoyl–(2'R,3'S)–3'–(p–chlorophenyl) isoserinate", Bioorganic and Medicinal Chemistry Letters, 2, 295–298 (1992).

Chaudhary, et al., "Unexpectedly Facile Hydrolysis of the 2–Benzoate Group of Taxol and Syntheses of Analogues with Increased Activities", Journal of American Chemical Society, 116, 4097–4098 (1994).

*Advanced Organic Chemistry,* Jerry March, Wiley & Sons, Third Edition, pp. 334–338.

2-DEBENZOYL-2-ACYL TAXOL DERIVATIVES AND METHOD FOR MAKING SAME

This application is a divisional of application Ser. No. 08/202,108, filed Feb. 25, 1994, now U.S. Pat. No. 5,703,247, which is a continuation in part of Ser. Nos. 08/029,759 and 08/030,612 both filed Mar. 11, 1993.

FIELD OF THE INVENTION

The present invention relates to 2-debenzoyl-taxol and methods for preparing same, 2-debenzoyl-2-acyl taxol analogues thereof, and methods for making same.

BACKGROUND OF THE INVENTION

The anti-cancer drug taxol 1 has shown excellent clinical activity against ovarian cancer and breast cancer and has also shown good activity against non-small cell lung cancer in preliminary studies. See "Taxol: A Unique Antineoplastic Agent With Significant Activity in an Advanced Ovarian Epithelial Neoplasms," Ann. Intern. Med., 111, 273–279 (1989), and "Phase II Trial of Taxol, an Active Drug in the Treatment of Metastatic Breast Cancer," J. Natl. Cancer Inst., 83, 1797–1805 (1991). Taxol was first isolated and its structure reported by Wani, et al, in "Plant Anti-Tumor Agents. VI. The Isolation and Structure of Taxol. A Novel Anti-Leukemic and Anti-Tumor Agent From Taxus Brevifolia," J. Am. Chem. Soc., 1971, 93, 2325. Taxol is found in the stem bark of the western yew, Taxus brevifolia, as well as in T. baccata and T. cuspidata. All references cited herein are incorporated by reference as if reproduced in full below.

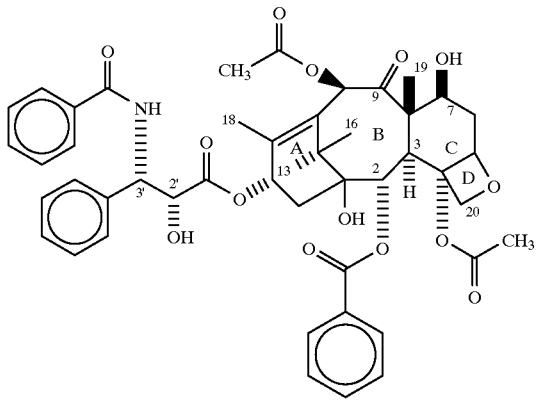

1

The preparation of analogues of taxol is an important endeavor, especially in view of taxol's clinical activity and its limited supply. The preparation of analogues might result in the synthesis of compounds with greater potency than taxol (thus reducing the need for the drug), compounds with superior bioavailability, or compounds which are easier to synthesize than taxol from readily available sources. Indeed, the synthesis of the taxol analogue taxotere 2, which differs from taxol only in the nature of the N-acyl substituent and in the absence of the 10-acetyl group, indicates the usefulness of this approach, since taxotere is reported to be approximately twice as active as taxol in some assays. See "Chemical Studies of 10-deacetyl Baccatin III. Hemisynthesis of Taxol Derivatives." Tetrahedron, 42, 4451–4460 (1986), and "Studies With RP56976 (taxotere): A Semi-Synthetic Analogue of Taxol." J. Natl. Cancer Inst., 83, 288–291 (1991).

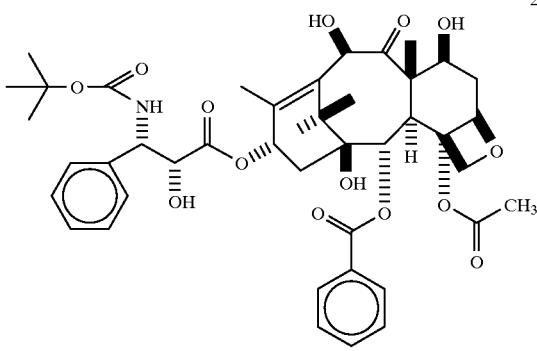

2

Numerous analogues of taxol having modifications of the C-13 side chain have been prepared. See U.S. Pat. No. 5,059,699. Many of the derivatives bearing modifications on the C-13 side chain have demonstrated anti-cancer activity. See for example: "The Chemistry of Taxol," Pharmac. Ther., 52, 1–34 (1991) and references therein, "Synthesis and Evaluation of some water-soluble prodrugs and derivatives of taxol with anti-tumor activity, J. Med, Chem., 35, 145–151 (1992), "Biologically Active Taxol Analogues with Deleted A-Ring Side Chain Substituents and Variable C-2' Configurations," J. Med. Chem., 34, 1176–1184 (1991), "Relationships Between the Structure of Taxol Analogues and Their Antimitotic Activity" J. Med. Chem., 34, 992–998 (1991).

Factors that contribute to the paucity of taxol congeners relative to their importance as anti-cancer agents include: the large size and complexity of these compounds, the presence of multiple reactive sites, and the presence of many stereospecific sites, which makes synthesis of even close analogues difficult. The large number of possible reaction mechanisms for even the simplest reactions leads to unpredictability of new reactions.

Although taxol has exhibited promising antineoplastic activity, there is a need for compounds which have even greater antineoplastic activity. It is believed that, by altering certain portions of the taxol structure, compounds with improved antineoplastic activity can be produced. Nevertheless, the aforementioned synthetic difficulties have prevented or at least slowed the development of more than only a few compounds, such as taxotere, which have similar or greater activity than taxol. Since it is believed that the tetracyclic taxane nucleus contributes to the antineoplastic activity of compounds incorporating same, it is desired to alter the ring substituents in order to develop derivatives of taxol and taxol analogues. Based on the previously noted studies, it is anticipated that such derivatives will have antineoplastic activity. Nevertheless, the complexity of taxol and its analogues makes it difficult to selectively alter certain substituents on the molecule. In particular, it has been previously impossible to selectively deacylate the C-2 position of taxol, and to produce taxol analogues modified at the C-2 position. Thus, there is a need for C-2 debenzoylated taxol analogues and congeners modified at the C-2 position, having antineoplastic activity, and intermediates thereof. There is also a need for methods for producing same and for using same to treat cancer. Since taxol and taxol analogues have low water solubility, there is a need to produce taxol analogues modified at the C-2 position having improved water solubility to aid in administration to cancer patients.

OBJECTS OF THE INVENTION

Thus, it is a primary object of this invention to produce taxol analogues which have a modified substituent at the C-2 position.

It is a further object of the present invention to provide taxol analogues having antineoplastic activity.

It is another object of this invention to produce taxol analogues that have improved in vivo activities for use as anti-cancer agents.

It is another object of the present invention to produce taxol analogues that have increased water solubility as compared with taxol.

It is yet another object of the present invention to make intermediates which are useful for producing taxol analogues having a modified substituent at the C-2 position. It is a further object to use taxol analogues which have a modified substituent at the C-2 position to treat cancer.

It is another object of this invention to provide methods for preparing derivatives of taxol and taxol analogues which have a modified substituent at the C-2 position.

SUMMARY OF THE INVENTION

The present application describes 2-debenzoyl taxol analogues, 2-debenzoyl-2-acyl taxol analogues, as well as procedures for preparing these compounds, and intermediates which can be utilized in preparing these compounds.

The compounds of the present invention may be used to treat patients suffering from cancer or as intermediates for making compounds which can be used to treat cancer. In a preferred embodiment, the taxol analogues have improved in vivo activities for use as anti-cancer agents. In another preferred embodiment, the taxol analogues have improved water solubility as compared with taxol.

Compounds of the present invention include compounds having the general formula:

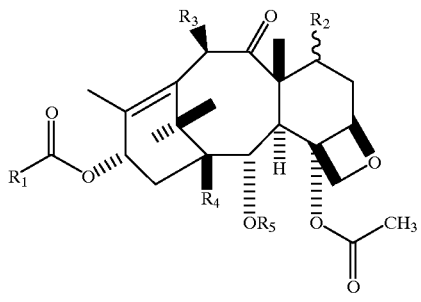

wherein $R_1$ is an alkyl or substituted alkyl; $R_5$ is selected from the group consisting of H and $C(O)R_a$; $R_2$ is selected from the group consisting of H, OH, oxyprotecting groups (i.e. triethylsilyloxy), $OR_b$, and $OC(O)R_b$; $R_3$ is selected from the group consisting of H, OH, and $OC(O)R_c$, and wherein $R_a$, $R_b$, and $R_c$ are independently selected from the group consisting of alkyls, substituted alkyls, alkenyls, alkynyls, aryls, and substituted aryls; provided that $R_a$ is other than phenyl and 3-hydroxyphenyl; and $R_4$ is H or OH.

Alternate embodiments of the above-described compounds include compounds:
wherein $R_2$ is OH or an oxyprotecting group;
wherein $R_5$ is H or $C(O)R_a$ and $R_a$ is an alkyl or a substituted aryl;
wherein $R_4$ is OH and/or wherein $R_1$ has the general formula:

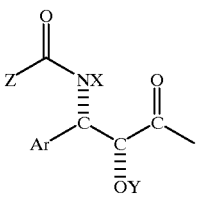

wherein Ar is an aryl; Z is selected from the group consisting of alkyls, alkenyls, alkynyls, alkoxys, and aryls; X is H or a protecting group, and Y is selected from the group consisting of H, protecting groups, alkyloyls, substituted alkyloyls, substituted aryloyls, and aryloyls.

Other preferred embodiments of the present invention include compounds having the formula:

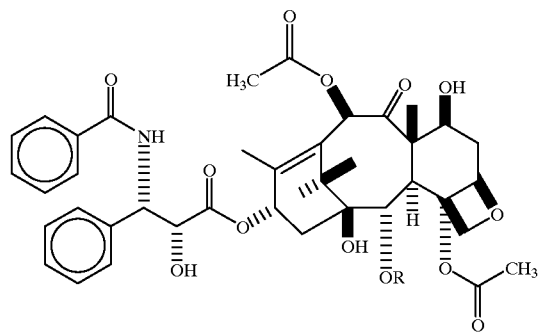

wherein R is selected from the group consisting of H and $C(O)R_a$ wherein $R_a$ is selected from the group consisting of alkyls, substituted alkyls, aryls, and substituted aryls; provided that $R_a$ is other than phenyl and 3-hydroxyphenyl.

Yet another preferred embodiment of the present invention includes compounds having the general formula:

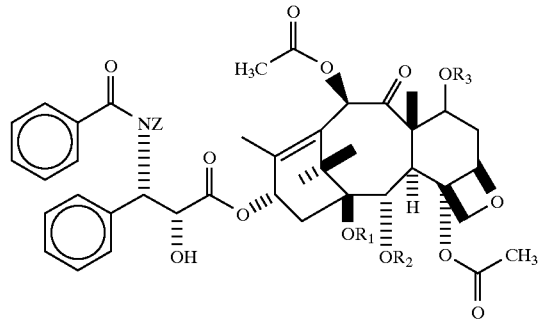

wherein Z is $C(O)OC(CH_3)_3$; $R_1$ is selected from the group consisting of H and $C(O)OC(CH_3)_3$; $R_2$ is selected from the group consisting of H and $C(O)R_a$ wherein $R_a$ is selected from the group consisting of alkyls, substituted alkyls, alkenyls, alkynyls, aryls (e.g. $C_6H_5$), and substituted aryls; and $R_3$ is a protecting group (e.g. triethylsilyl, $C(O)OC(CH_3)_3$), or hydrogen.

Yet another preferred embodiment of the present invention comprises pharmaceutical compositions, which comprise an antineoplastically effective amount of at least one of the compounds described above.

The present invention also contemplates a method for treating cancer comprising the administration of an antineoplastically effective amount of at least one of the compounds described herein.

Another preferred embodiment of the present invention comprises a method of making a first compound having the general formula:

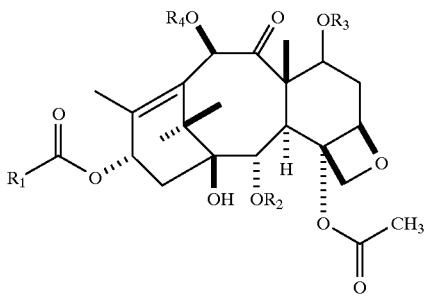

wherein $R_1$ is an alkyl or substituted alkyl; $R_2$ is selected from the group consisting of H and $C(O)R_a$; $R_3$ is selected from the group consisting of H, protecting groups, $R_b$, and $C(O)R_b$; $R_4$ is selected from the group consisting of H and $C(O)R_c$, and wherein $R_a$, $R_b$, and $R_c$ are independently selected from the group consisting of alkyls, substituted alkyls, alkenyls, alkynyls, aryls, and substituted aryls; provided that $R_a$ is other than phenyl and 3-hydroxyphenyl; comprising the step of replacing a moiety situated at the C-2 position of a second compound wherein said second compound is selected from the group consisting of taxol and taxol analogues.

For example, the foregoing method may be employed wherein said second compound has the general formula:

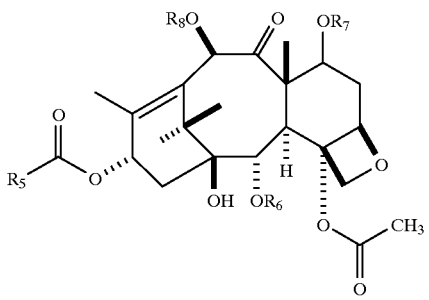

wherein $R_5$ is an alkyl or substituted alkyl; $R_6$ is selected from the group consisting of H and $C(O)R_d$; $R_7$ is selected from the group consisting of H, protecting groups, $R_b$, and $C(O)R_a$; $R_b$ is selected from the group consisting of H and $C(O)R_c$, and wherein $R_d$, $R_e$, and $R_c$ are independently selected from the group consisting of alkyls, substituted alkyls, alkenyls,, alkynyls,, aryls,, and substituted aryls;

and further comprising a step wherein said second compound is reacted with lithium hydroxide;

and further comprising a reaction with an acylating agent, followed by the step of deprotection;

wherein the deprotection step comprises a reaction with formic acid; and wherein said acylating agent comprises a reagent selected from the group consisting of acid halides, β-lactams, anhydrides, and carboxylic acids.

In another embodiment of the method described above said first compound has the formula:

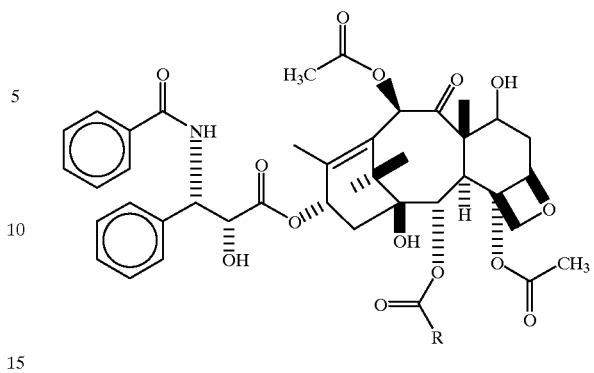

wherein R is selected from the group consisting of alkyl, substituted alkyl, aryl, and substituted aryl;

and wherein said second compound is taxol;

further comprising the step of reacting with di-t-butyl dicarbonate.

The second compound is thus converted into a compound having the formula:

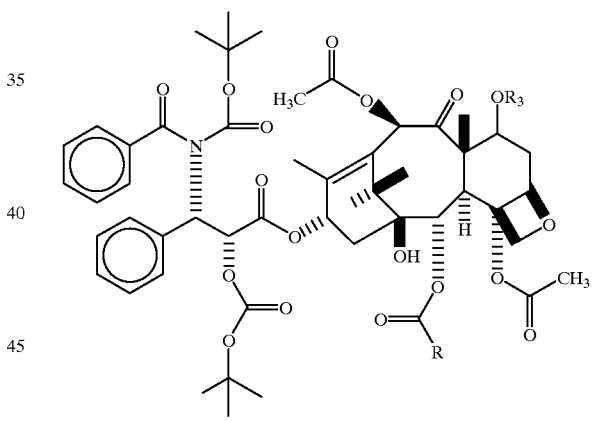

wherein $R_3$ is a protecting group and R is selected from the group consisting of alkyl, substituted alkyl, aryl, and substituted aryl.

The method further comprises the step of deprotection; said deprotection step occurring subsequent to the step of adding an acylating agent; and wherein said deprotection step comprises the addition of formic acid.

The present invention also discloses a method for making a first compound having the formula:

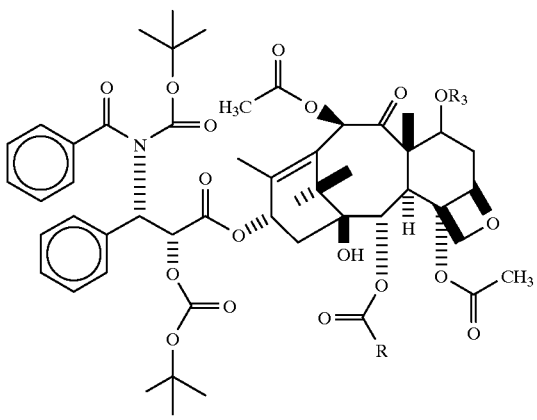

wherein $R_3$ is a protecting group and R is selected from the group consisting of alkyl, substituted alkyl, aryl, and substituted aryl.

The present invention also comprises analogues of taxol in which the benzoyl group has been replaced by an acyl, $C(O)R_a$, wherein $R_a$ is selected from the group consisting alkyl, substituted alkyl, alkenyl, alkynyl, aryl, and substituted aryl;

provided that $R_a$ is not phenyl or 3-hydroxyphenyl.

Another preferred embodiment of the present invention includes a method for making taxol analogues having a hydroxy or acyloxy substituent, other than benzoyloxy and 3-hydroxybenzoyloxy, at the C-2 position of the B-ring of the taxane tetracyclic nucleus comprising the step of removing a benzoyl moiety from said C-2 position of a taxol congener having a benzoyloxy group at said C-2 position.

In a variation of the above-described method, said taxol analogues have the general formula:

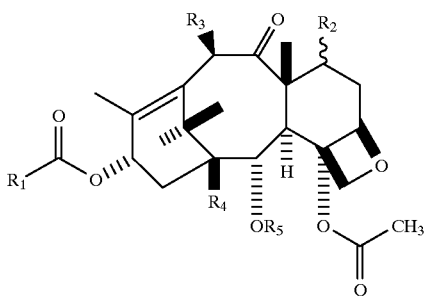

wherein $R_1$ is an alkyl or substituted alkyl; $R_5$ is selected from the group consisting of H and $C(O)R_a$; $R_2$ is selected from the group consisting of H, OH, oxyprotecting groups, $OR_b$, and $C(O)R_b$; $R_3$ is selected from the group consisting of H, OH, and $OC(O)R_c$, and wherein $R_a$, $R_b$, and $R_c$ are independently selected from the group consisting of alkyls, substituted alkyls, alkenyls, alkynyls, aryls, and substituted aryls; provided that $R_a$ is other than phenyl and 3-hydroxyphenyl; and $R_4$ is H or OH.

The subject matter of the present application includes taxol analogues comprising a substituted benzoyloxy substituent at the C-2 position. Non-limiting examples include meta-substituted benzoyls, meta- and para-substituted benzoyls, and ortho-substituted benzoyls. Analogues in which a heterocyclic moiety replaces the phenyl ring of the benzoyl moiety are also disclosed. Certain non-limiting examples of such compounds are shown in Table I, compounds 13a, 13c–13t, and 13y–13ee. Certain, non-limiting preparative methods are also described herein. The present invention also contemplates the use of these compounds in the treatment of cancer.

In a preferred embodiment of the present invention, it has been surprisingly discovered that, by acylating the C-2 hydroxyl of a taxol analogue with 3,5-fluorobenzoic acid, followed by deprotection of the resulting compound, a compound having about 25,000 times taxol's antineoplastic activity as determined by a cell culture assay is formed. The compound prepared is shown below:

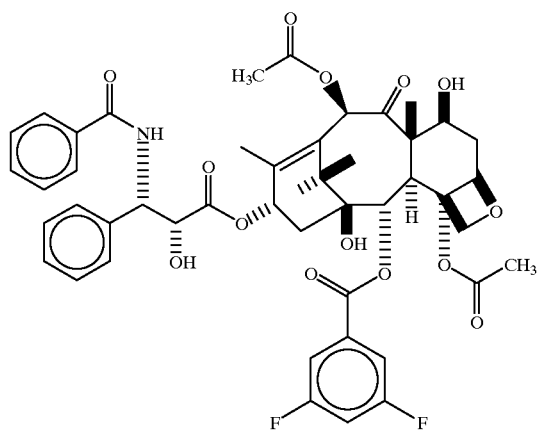

The compounds of the present invention may be used to treat patients suffering from cancer or as intermediates for making compounds which can be used to treat cancer. In a preferred embodiment, the taxol analogues have improved in vivo activities for use as anti-cancer agents. In another preferred embodiment, the taxol analogues have improved water solubility as compared with taxol.

In a preferred embodiment, compounds of the present invention are taxol or taxol congeners having a meta-substituted benzoyloxy group at the C-2 position of the B-ring of the tetracyclic nucleus. Preferred meta-substituents include, but are not limited to halogens (e.g., chlorine, bromine, fluorine, iodine), alkoxys (e.g., methoxy, ethoxy, etc.), diatomic species (e.g., CN, NC, etc.), linear triatomic species (e.g., $N_3$, NCO, etc.), and azido containing moieties. The meta-substituted benzoyloxy group may additionally comprise a (non-hydrogen) para-substituent and/or ortho-substituents.

Another preferred embodiment of the present invention involves compounds having the general formula:

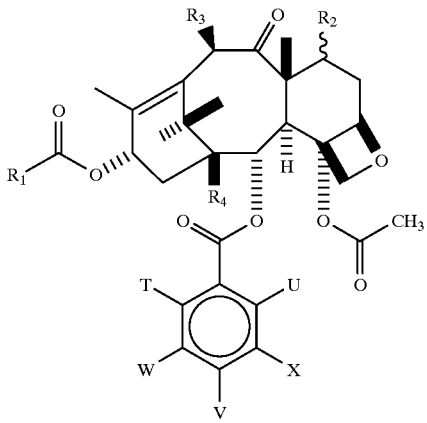

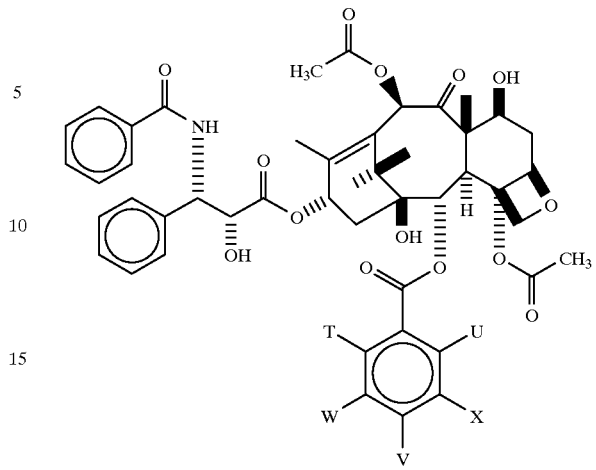

wherein $R_1$ is an alkyl or a substituted alkyl, $R_2$ is selected from the group consisting of H, OH, alkyloxy, aryloxy, oxyprotecting groups (e.g. triethylsilyloxy) and $OC(O)R_a$, $R_3$ is selected from the group consisting of H, OH, and $OC(O)R_b$, wherein $R_a$ and $R_b$ can be the same or different and are selected from the group consisting of alkyls, substituted alkyls, alkenyls, alkynyls, aryls, and substituted aryls, wherein T, U, W, V, and X are any substituents, provided that T, U, W, V, and X are not all H and when T, U, W, and V are H, X is other than OH and when T, U, V, and X are H, W is other than OH; and $R_4$ is H or OH.

Other preferred embodiments of the present invention include the compound having the general formula described above wherein:

$R_1$ has the general formula:

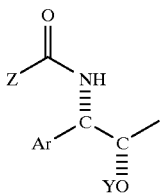

in which Ar is an aryl; Z is selected from the group consisting of alkyls, alkenyls, alkynyls, alkoxys, (e.g. $OC(CH_3)_3$) and aryls (e.g. $C_6H_5$); and Y is selected from the group consisting of H, protecting groups, alkyloyls, and aryloyls; and T, U, W, V, and X are independently selected from the group consisting of hydrogens, halogens, alkoxys, diatomics, and linear triatomics.

Alternatively, X may be selected from the group consisting of alkyls, substituted alkyls, alkenyls, alkynyls, aryls, and substituted aryls.

In many preferred embodiments, $R_1$ is the substituted alkyl appearing at the C-13 side-chain of taxol.

Particularly preferred compounds have the general formula:

wherein T, U, V, W, and X are any substituents provided that T, U, V, W, and X are not all H and when T, U, V, and W are H, X is not OH, and when T, U, V, and X are H, W is not OH.

Alternative preferred embodiments of the present invention include the compounds having the general formula described above wherein X is selected from the group consisting of alkyls, substituted alkyls, alkenyls, alkynyls, aryls, substituted alkyls, amides, amines, nitros, and carboxylates; or wherein T, U, V, W, and X are all fluorine.

The present invention contemplates methods of treating cancer comprising the administration of an antineoplastically effective amount of any of the taxol analogues described herein.

The present invention also provides a method for making a first compound having the formula:

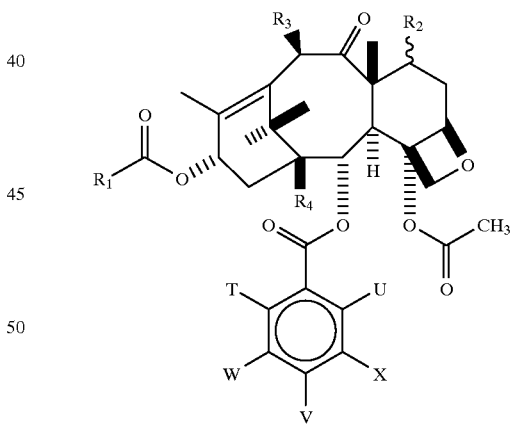

wherein $R_1$ is an alkyl or a substituted alkyl, $R_2$ is selected from the group consisting of H, OH, alkoxy, aryloxy, oxyprotecting groups and $OC(O)R_a$, and $R_3$ is selected from the group consisting of H, OH, and $OC(O)R_b$, wherein $R_a$ and $R_b$ can be the same or different and are selected from the group consisting of alkyls, substituted alkyls, alkenyls, alkynyls, aryls, and substituted aryls, and $R_4$ is H or OH; and T, U, V, W, and X are any substituents, provided that T, U, V, W, and X are not all H and when T, U, V, and W are H, X is not OH, and when T, U, V, and X are H, W is not OH;

comprising a step wherein the benzoyl moiety at the C-2 position of a second compound having the formula:

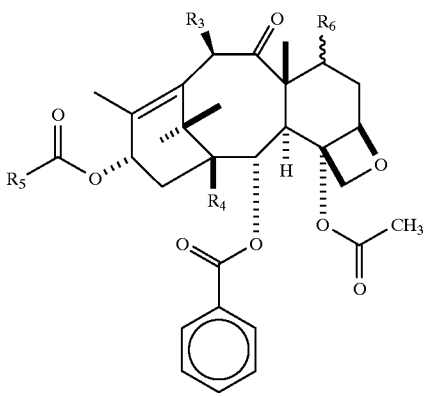

wherein $R_4$ is H or OH, $R_5$ is an alkyl or a substituted alkyl, $R_6$ is selected from the group consisting of H, OH, alkyloxy, aryloxy, oxyprotecting groups (e.g. triethylsilyloxy) and $OC(O)R_a$, and $R_3$ is selected from the group consisting of H, OH, and $OC(O)R_b$, wherein $R_a$ and $R_b$ can be the same or different and are selected from the group consisting of alkyls, substituted alkyls, alkenyls, alkynyls, and aryls;

is replaced by a substituted benzoyl moiety provided that if both ortho-substituents, the para-substituent, and one meta-substituent on said benzoyl moiety are H, the other meta-substituent is other than H or OH.

Alternative preferred embodiments of the method of making said first compound, described above, include:

wherein $R_1$ has the general formula:

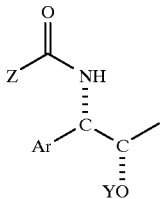

wherein Ar is an aryl; Z is selected from the group consisting of alkyls, alkenyls, alkynyls, alkoxys, (e.g. $OC(CH_3)_3$), and aryls (e.g. $C_6H_5$); and Y is selected from the group consisting of H, protecting groups, alkyloyls, and aryloyls;

wherein T, U, V, and W are H and X is selected from the group consisting of halogens, diatomics and linear triatomics; and wherein Y in said second compound is triethylsilyl and $R_6$ is triethylsilyloxy and further wherein said second compound is debenzoylated via reaction in a mixture comprising aqueous sodium hydroxide, a phase-transfer catalyst, and an organic solvent, to yield a compound having a hydroxyl at the C-2 position, wherein said compound having a hydroxyl at the C-2 position is reacted in a subsequent step with meta-$C_6H_4X$—COOH.

DEFINITIONS

Unless clearly indicated by context or statement to the contrary, the terms used herein have the meanings as conventionally used in the chemical arts, and definitions incorporate those used in standard texts, such as but not limited to *Grant & Hackh's Chemical Dictionary*, 5th edition, McGraw-Hill, 1987; Streitwieser et al., *Introduction to Organic Chemistry*, 2nd edition, Macmillan, 1981; and March, *Advanced Organic Chemistry*, 3rd edition, Wiley, 1985.

The term alkyl refers to straight-chain or branched-chain hydrocarbons. In some preferable embodiments, alkyl refers to the lower alkyls containing from one to six carbon atoms in the principal chain and up to 10 carbon atoms; the lower alkyls may be straight or branched chain and by way of non-limiting example include methyl, ethyl, propyl, isopropyl, butyl, isobutyl, tert-butyl, and the like.

The term substituted alkyl refers to groups including, but not limited to, the alkyl groups discussed above which have as substituents halo (e.g., chloro, bromo), nitro, sulfate, sulfonyloxy, carboxy, carboxylate, phosphate (e.g., $OP(O)(OH)_2$, $OP(O)(OR)(OH)$), carbo-lower-alkoxy (e.g., carbomethoxy, carboethoxy), amino, mono- and di-lower-alkylamino (e.g., methylamino, dimethylamino, carboxamide, sulfonamide, diethylamino, methylethylamino,) amide lower-alkoxy (e.g., methoxy, ethoxy), lower-alkanoyloxy (e.g., acetoxy), alkenyl, alkynyl, aryl, aryloxy, and combinations of these (e.g., alkylbenzenesulfonates).

The term aryl has the meaning known in the chemical arts, and aryl also refers to heterocyclic aryls. Substituted aryls have the same substituents discussed above for the substituted alkyls and also include, but are not limited to, aryls having lower alkyl substituents such as methyl, ethyl, butyl, etc.

The use of the term "any substituent" in the present application refers only to those substituents capable of bonding to the C-2 position of the taxane tetracyclic nucleus and which are not incompatible with the remainder of the taxol analogue structure (i.e. not so large as to preclude bonding to the C-2 position, or not so reactive as to lead to rapid decomposition of the structure of the taxol or taxol analogue). The term "analogues of taxol" refers to compounds comprising the taxane tetracyclic nucleus and an acetyl group at the C-4 position.

In the context of the present invention, protecting groups can be used to protect hydroxyls, or the NH group of an amide.

DETAILED DESCRIPTION OF THE INVENTION

The present invention pertains to the removal of the benzoyl group at the C-2 position of taxol and taxol analogues, thus resulting in a 2-debenzoyl taxol analogue. The 2-debenzoyl taxol analogues can be reacylated with acylating agents to produce 2-debenzoyl-2-acyl taxol analogues.

Figure 1:
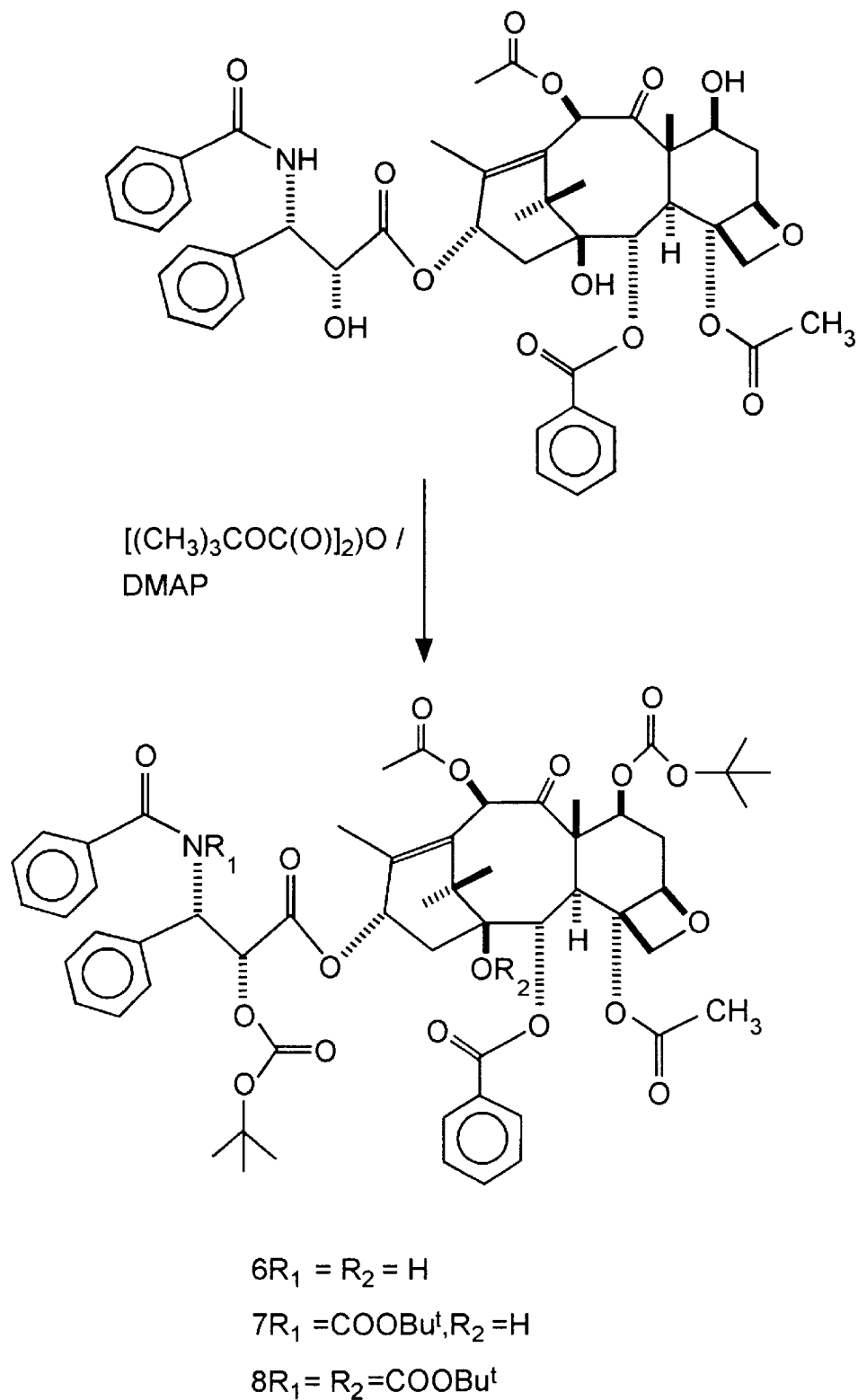
FIG. 1 illustrates the reaction of taxol with excess di-tert-butyl-dicarbonate in the presence of 4-dimethylaminopyridine (DMAP) to yield 2',7-di(t-butoxycarbonyloxy) taxol, 2',7,N-tri(t-butoxycarbonyloxy) taxol, and 1,2',7,N-tetra(t-butoxycarbonyloxy) taxol.

As illustrated in FIG. 1, treatment of taxol [1] with excess di-tert-butyl-dicarbonate ($BOC_2O$) in the presence of 4-dimethylaminopyridine (DMAP) converts it a over a period of five days to a mixture of 2',7-di(t-BOC)taxol [6], 2',7,N-tri(t-BOC)taxol [7], and 1,2',7,N-tetra(t-BOC)taxol [8] (t-BOC is tert butoxycarbonyl).

Compound 8 could be isolated after careful work-up that avoids acidic conditions, but it was most conveniently converted into the tri(t-BOC)taxol [7] by a mild acid treatment during work up. Using this procedure the tri(t-BOC) taxol [7] could be obtained in 41% yield and the di(t-BOC) taxol [6] in 32% yield, for a combined yield of 73%.

Figure 2:
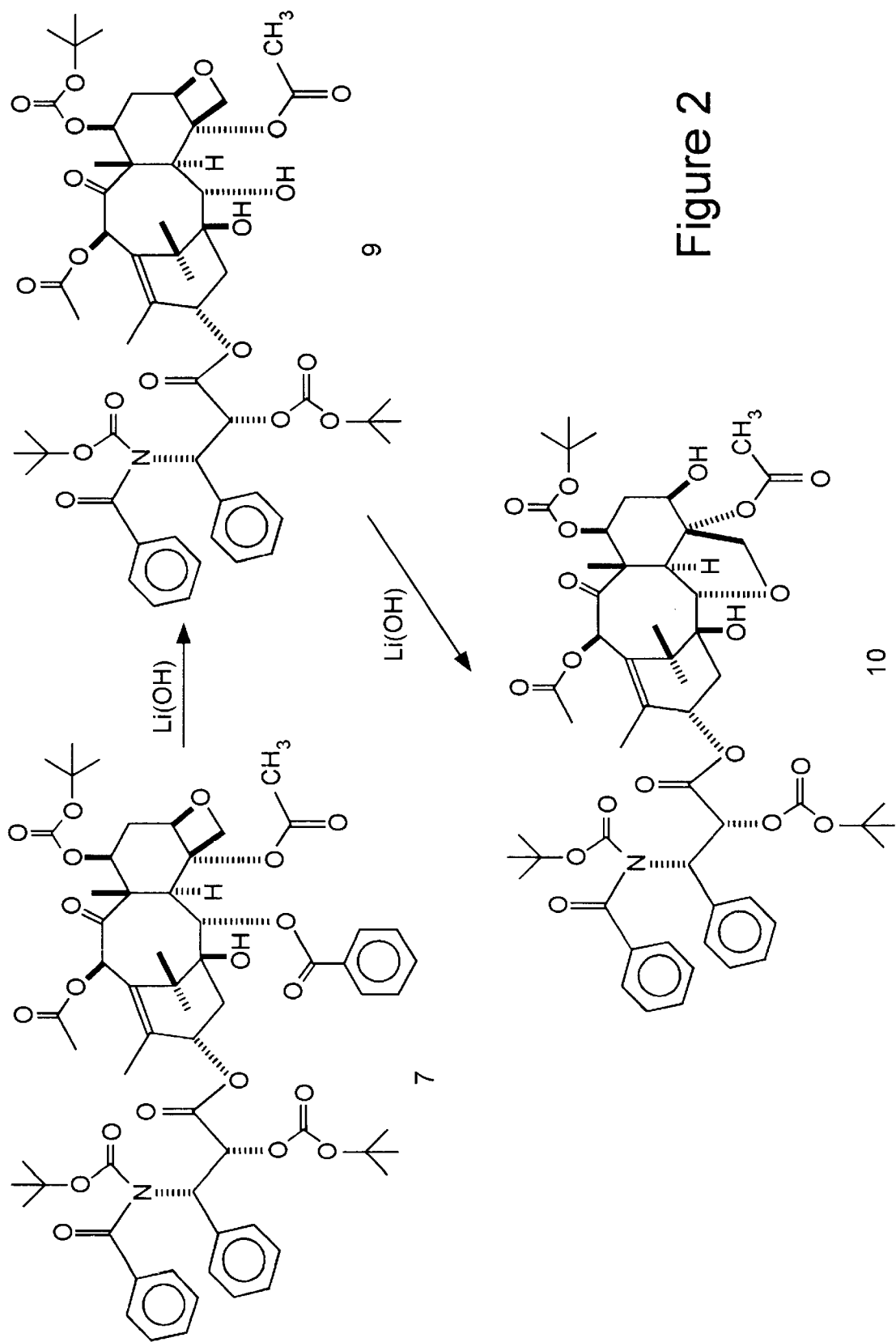
FIG. 2 illustrates the reaction of 2',7,N-tri(t-butoxycarbonyloxy) taxol with LiOH to yield 2',7,N-tri(t-butoxycarbonyloxy)-2-debenzoyl taxol; and prolonged reaction resulting in cleavage of the D-ring of the taxane skeleton.

It has been surprisingly discovered that treatment of taxol analogues, in which the C-2' and C-7 positions have been protected with t-BOC groups with lithium hydroxide results in selective hydrolysis at the C-2 position. For example, with reference to FIG. 2, treatment of 2',7,N-tri(t-BOC)taxol with lithium hydroxide converted it into 2',7,N-tri(t-BOC)-2-debenzoyltaxol [9].

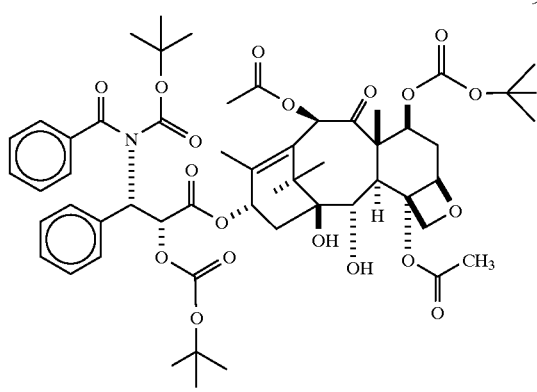

9

In this process the 2-benzoyl group is cleaved, but the t-BOC groups are not cleaved and neither are any of the other ester functions. If reaction with lithium hydroxide is prolonged, conversion of 9 into the rearranged product 10 occurs, and it has not so far been possible to obtain 9 without some formation of 10.

Conversion of 2', 7,N-tri-(t-BOC) -2-debenzoyltaxol [9] into 2-debenzoyltaxol was not possible with conventional t-BOC cleavage agents, because rearrangement occurs simultaneously with deprotection to yield the isotaxol 11.

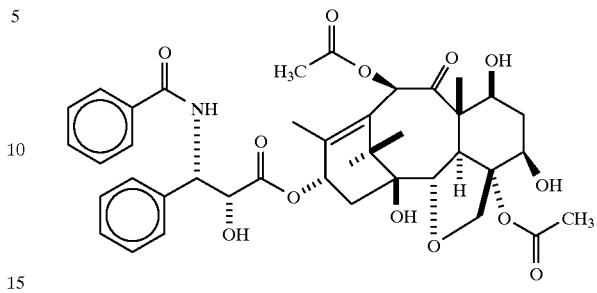

11

Figure 3:
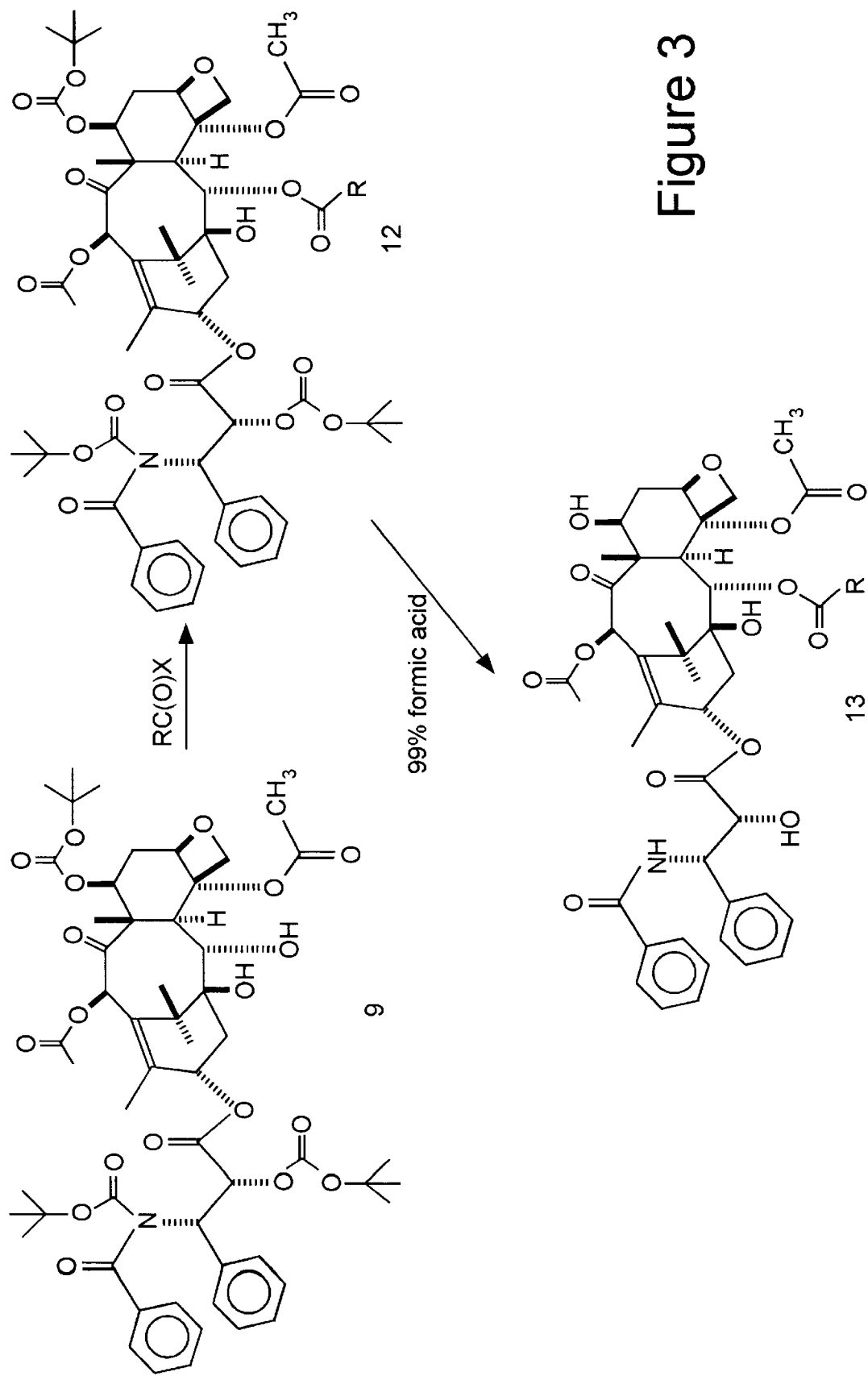
FIG. 3 illustrates the reaction of 2',7,N-tri(t-butoxycarbonyloxy)-2-debenzoyl taxol with an acylating agent to yield 2',7,N-tri(t-butoxycarbonyloxy)-2-debenzoyl-2-acyl taxol, followed by removal of the oxyprotecting groups with formic acid to yield 2-debenzoyl-2-acyl taxol.

FIG. 3 illustrates, by way of a non-limiting example, preparation of 2-debenzoyl-2-acyl taxols by reacylation of the debenzoyl derivative 9 with a desired acyl group to yield the protected derivative 12. Deprotection of 12 with 99% formic acid (13) then yields the taxol analogue 13.

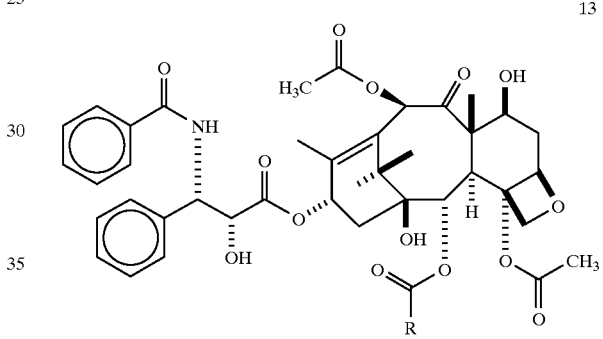

13

Figure 4:
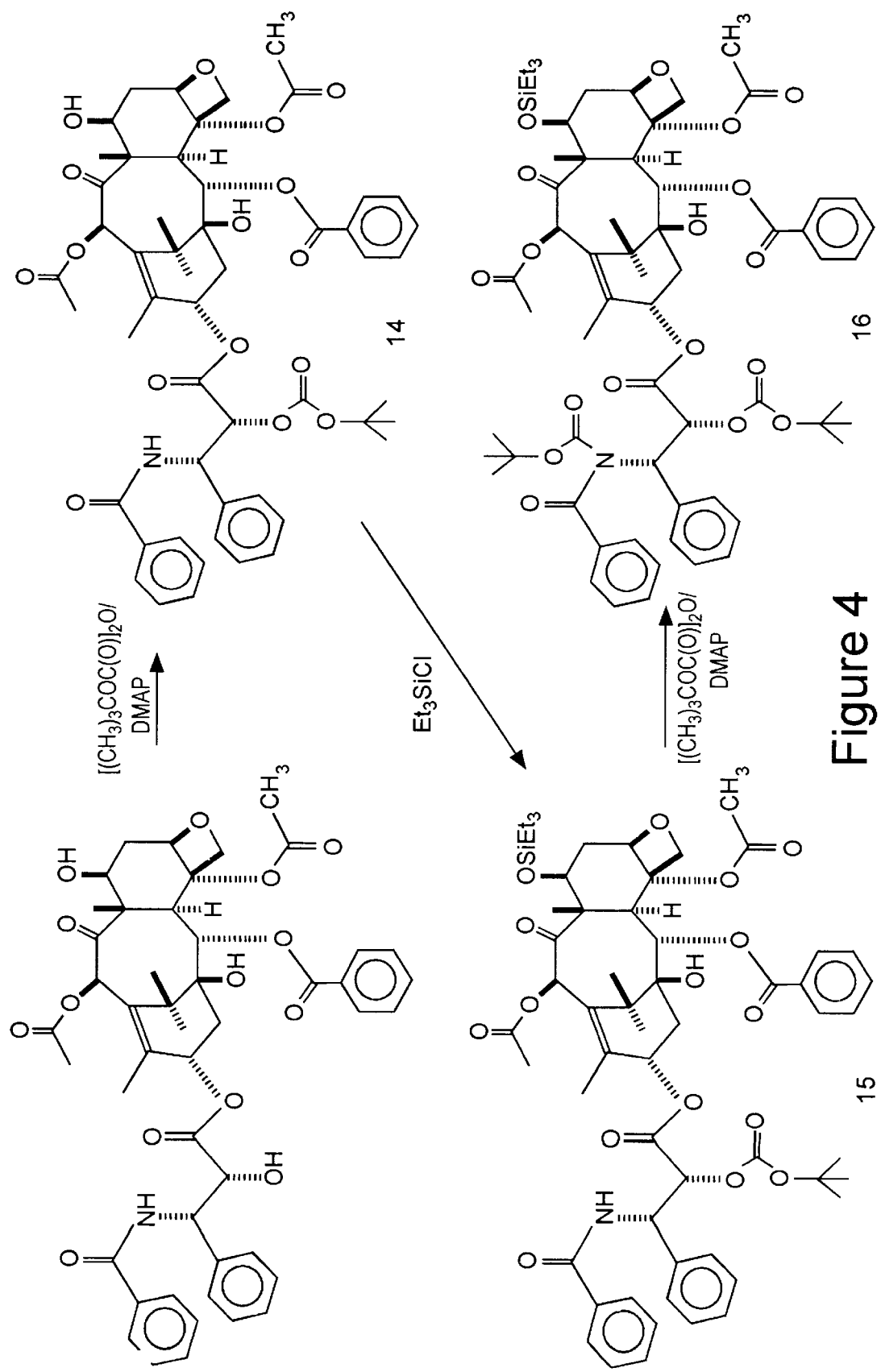
FIG. 4 illustrates the reaction of taxol with one equivalent of di-tert-butyl dicarbonate in the presence of 4-dimethylaminopyridine to yield the 2'-t-butoxycarbonyloxy derivative of taxol followed by reaction with triethylsilyl chloride to yield 2'-t-butoxycarbonyloxy-7-triethylsilyltaxol, and the subsequent reaction with an excess of di-t-butyl dicarbonate to yield 2',N-di-t-butoxycarbonyloxy-7-triethylsilyl taxol.
Figure 5:
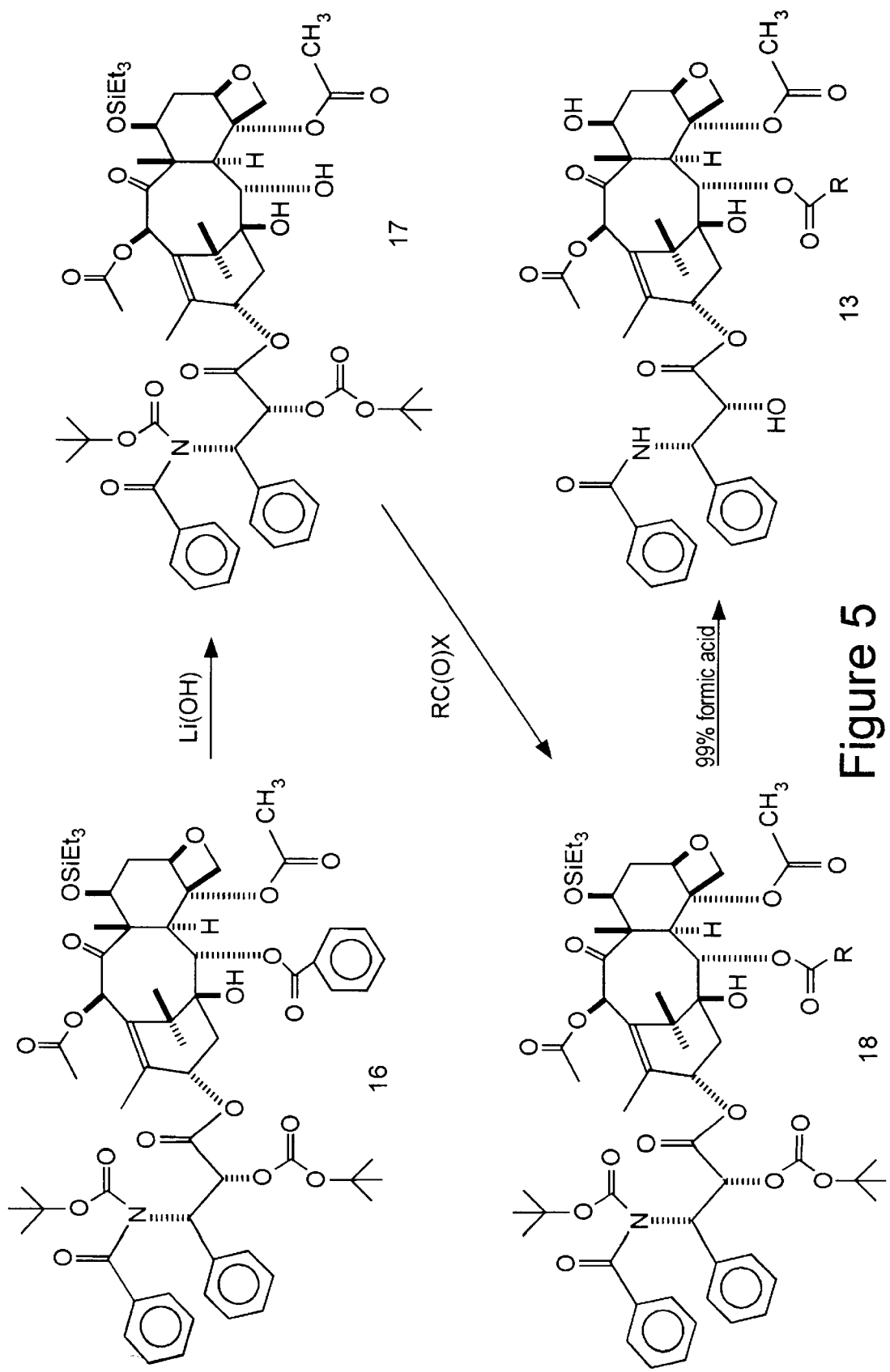
FIG. 5 illustrates the reaction of 2',N-t-butoxycarbonyloxy-7-(triethylsilyl)taxol with lithium hydroxide to yield 2',N-di-t-butoxycarbonyloxy-2-debenzoyl-7-(triethylsilyl) taxol followed by reaction with an acylating agent and subsequent deprotection with formic acid to yield 2-debenzoyl-2-acyl taxol.

A second process for the preparation of 2-debenzoyl-2-acyl taxols involves the selective protection of the C-7 position with a protecting group such as a triethylsilyl. A preferred embodiment of a second process for the synthesis of C-2 analogues of taxol is illustrated in FIGS. 4 and 5. Taxol is first converted to its 2'-t-BOC derivative 14, and this is treated with triethylsilyl chloride to give the 2'-t-BOC, 7-triethylsilyl derivative 15. Finally 15 is treated again with di-t-butyl dicarbonate to give the N-t-BOC, 2'-t-BOC, 7-triethylsilyl derivative 16.

The taxol derivative 16 can be debenzoylated as described earlier to give the 2-debenzoyl analogue 17. Reacylation of 17 with a desired acyl group then yields the acyl derivative 18, where C(O)R is any desired acyl group. Deprotection of 18 with 99% formic acid then gives a 2-debenzoyl-2-acyltaxol derivative 13. One example of this chemistry is the conversion of 17 back to taxol by benzoylation to the benzoyl derivative 16 and deprotection to yield taxol. Reaction of 17 with 3-(3-(trifluoromethyl)-3H-diazirin-3-yl phenoxyacetic acid yields 2',N-di(t-BOC)-7-(triethylsilyl-2-debenzoyl-2(3-(3-trifluoromethyl)-3H-diazirin-3-yl) phenoxyacetyltaxol, which can be subsequently deprotected to yield the compound shown below.

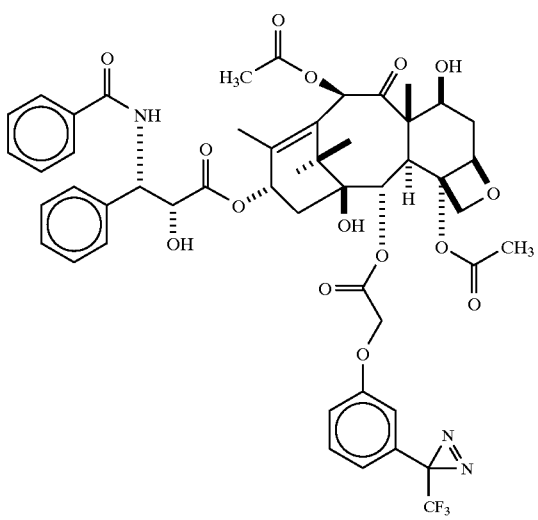

Figure 6:
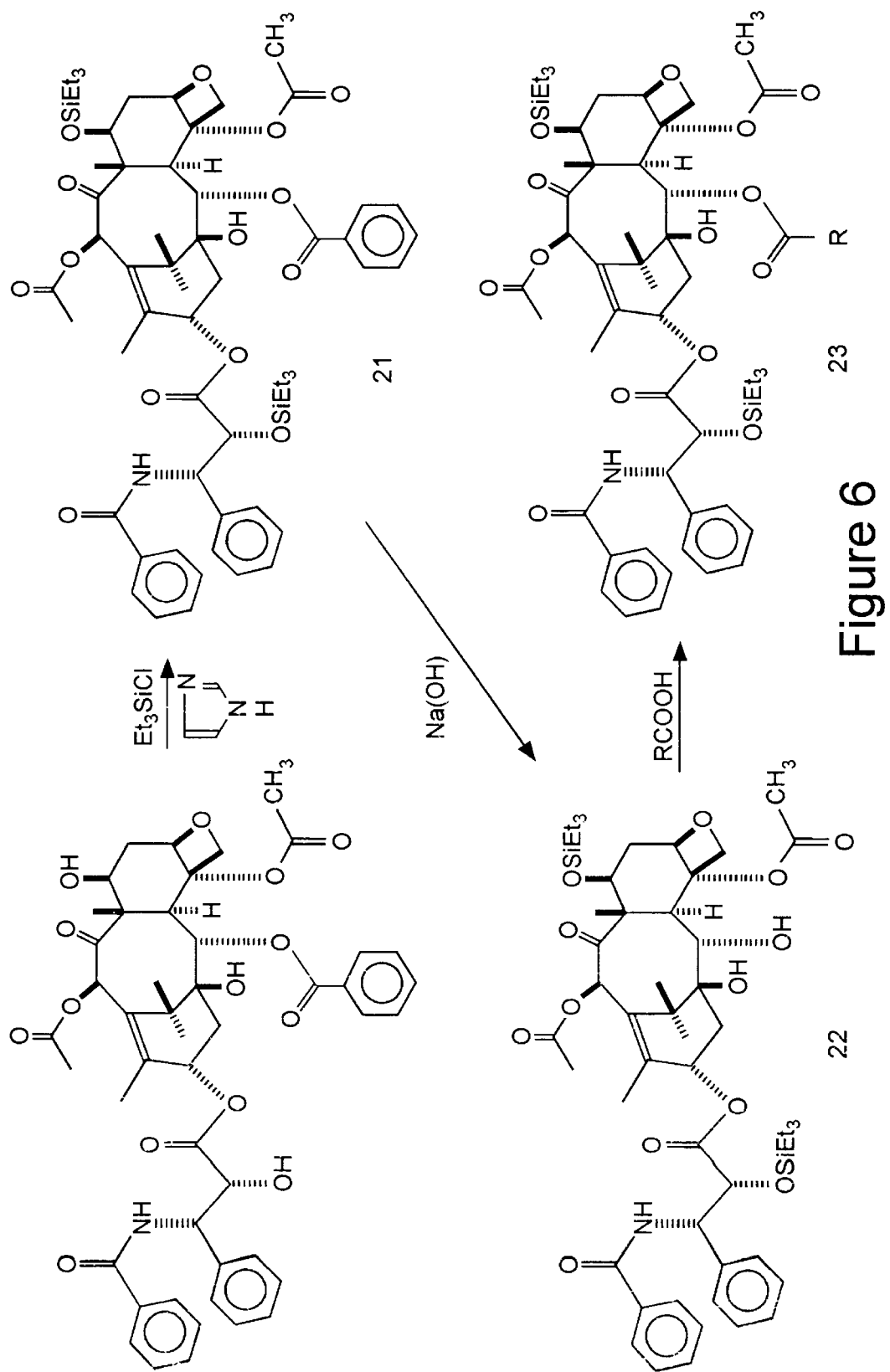
FIG. 6 illustrates the reaction of taxol with triethylsilyl chloride in the presence of imidazole to yield 2',7-(triethylsilyl) taxol, followed by reaction with sodium hydroxide under phase-transfer conditions to yield 2-debenzoyl-2',7-(triethylsilyl) taxol followed by reaction with a carboxylic acid to yield 2-debenzoyl-2',7-triethylsilyl-2-acyl taxol.

In a particularly advantageous process for the preparation of 2-debenzoyl-2-acyl taxol analogues, the substituent at the C-2 position is converted from an acyl to a hydroxy by base catalyzed hydrolysis under phase transfer conditions. An embodiment of this preferred process for the preparation of 2-debenzoyl-2-acyl taxol analogues is illustrated in FIG. 6. Conversion of taxol 1 to its 2',7-di(triethylsilyl) derivative 21 proceeds smoothly and in good yield on treatment of taxol with triethylsilyl chloride and imidazole in DMF. The key reaction is thus the hydrolysis of 21 under phase-transfer conditions with aqueous sodium hydroxide. This converts 21 to 2',7-di-(triethylsilyl)-2-debenzoyltaxol 22. Acylation of 22 with an appropriate benzoic, or substituted benzoic, or other carboxylic acid then gave the protected 2-debenzoyl-2-acyltaxol analogue 23, which could be deprotected readily to the 2-debenzoyl-2-acyltaxol 13.

Acylation of 22 with various aromatic carboxylic acids in the presence of dicyclohexylcarbodiimide and 4-pyrrolidinopyridine has led to the preparation of various 2-debenzoyl-2-acyl taxols 13. As shown in Table 1, the activities of several 2-debenzoyl-2-acyltaxols were determined in a cell culture assay using P-388 lymphocytic leukemia cells, and compared with that of taxol; compounds with an $ED_{50}/ED_{50}$(taxol) value of less than 1 are more active than taxol in this assay. For details of the cell culture assay, see Abbott, B. J., "Protocol 14 of Instruction 275," National Cancer Institute, National Institutes of Health, Jan. 24, 1978.

It was found that compounds lacking the benzoyl group, such as [13b], were less active or about as active as taxol. Of particular significance compounds with an ortho-substituted benzoyl group, such as 13o, were found to have increased bioactivity as compared with taxol. Of particular significance is the discovery that compounds with a meta-substituted benzoyl group have much greater biological activity than taxol [13c, 13d, 13f]. For example, 2-debenzoyl-2-(m-azidobenzoyl)taxol [13f] shows activity against P-388 leukemia in vitro that is 500 times higher than that of taxol. The co-pending application also discloses that compounds with fluoro substituted benzoyls have especially high biological activity; for example 2-debenzoyl-2-(3,5-difluorobenzoyl)taxol [13t] shows activity against P-388 leukemia in vitro that is 25,000 times higher than that of taxol. The compounds disclosed in the co-pending U.S. application are thus highly promising candidates for use as anticancer drugs when administered in an antineoplastically effective amount to patients suffering from cancer.

Having shown the preparation of 2-debenzoyl taxols and 2-debenzoyl-2-(acyl) taxols, additional non-limiting preferred embodiments of this invention include congeners of 2-debenzoyl taxols and 2-debenzoyl-2-(acyl)taxols in which various modifications are made to the taxol structure, such as, but not limited to, varying substituents at the C-1 position, C-7 position, C-10 position and/or the C-13 side chain.

Particularly desired modifications include, but are not limited to, modifications which increase water solubility or stability of the 2-debenzoyl-2-(meta-substituted benzoyl) taxols and taxol congeners. Non-limiting examples of such water soluble derivatives can be produced by the methods disclosed in U.S. Pat. Nos. 5,059,699 and 4,942,184; the solubilizing groups described therein can likewise be attached to compounds of the present invention to increase their water solubility.

It is known that the C-7 hydroxyl group on taxol and Baccatin III can be readily epimerized, and that epimerization has little effect on bioactivity. See "The Chemistry of Taxol," *Pharmac. Ther.*, 52, 1–34 (1991). It is therefore to be understood that this invention contemplates either or both C-7 enantiomers in the compounds of the present invention. Nonetheless, it is often preferred to prevent epimerization of the C-7 hydroxyl and in the Examples of the present invention epimerization is avoided by protecting the C-7 hydroxyl prior to exposing taxol or its analogues to conditions which catalyze epimerization.

In addition to the acylations and acyloxy to hydroxy conversions at the C-7 and C-10 positions, of which certain embodiments are exemplified in the literature; this invention also contemplates the removal of the oxy group(s) from the C-1, C-7, and/or C-10 positions. Certain, preferred embodiments of these removals are described below.

10-deacetoxytaxol can be prepared by treatment of 7-(triethylsilyl)-10-deacetylbaccatin III with carbon disulfide, methyl iodide, and sodium hydride to yield the 10-(methylxanthyl) derivative. Treatment of this with tributyltin hydride (TBTH) and azobisisobutyronitrile (AIBN) yields 7-(triethylsilyl)-10-deacetoxybaccatin III, which can be esterified with the taxol side-chain as previously disclosed. (Highly efficient, practical approach to natural taxol, *J. Am. Chem. Soc.*, 1988, 110, 5917–5919). Treatment of this 10-deacetoxytaxol as described for taxol itself then converts it to the 10-deacetoxy-2-debenzoyl-2-acyl taxol analogues described.

7-deoxytaxol can be made by treatment of 2'-triethylsilyltaxol with sodium hydride, carbon disulfide, and methyl iodide to give the 7-(methylxanthyl) derivative, which is then deoxygenated with TBTH, and AIBN to yield 2'-(triethylsilyl)-7-desoxytaxol. This is then converted to its 2-debenzoyl-2-acyl derivative as previously described for taxol.

It is contemplated that 1-deoxytaxol can be made by treating 2',7-di(triethylsilyl)taxol with 2N NaOH in the presence of carbon disulfide, methyl iodide, benzene, and a phase-transfer catalyst, to give the 1-(methylxanthyl)-2-debenzoyl derivative. Acylation with a suitable substituted benzoic acid then yields the corresponding 2-aroyl derivative, which can be reduced to the 1-deoxy derivative with TBTH and AIBN. Deprotection of the 2'- and the 7-positions then gives a 1-desoxy-2-debenzoyl-2-aroyl taxol derivative.

In addition to the described alterations to the C-2 position, the C-2 position can also be converted to a methylene. For example, 1-benzoyl-2-deoxytaxol can be prepared by treating 2',7-di(triethylsilyl)taxol with sodium hydride, carbon disulfide, and methyl iodide, to yield 1-benzoyl-2-(methylxanthyl)2',7-di(triethylsilyl)taxol: the benzoyl group is transferred from the C-2 to the C-1 position during this reaction. Deoxygenation with AIBN and TBTH followed by removal of the 2',7-TES groups then yields 1-benzoyl-2-deoxytaxol.

METHODS AND MATERIALS

Specific reaction methods are described in more detail in the following non-limiting examples. Certain methods used herein are generally described in the "*Journal of Organic Chemistry,*" 51, pp. 797–802 (1986). Low resolution mass spectrometry data were obtained on a VG 7070 E-HF mass spectrometer. All technical and scientific terms used herein have the same meaning as commonly understood by one of ordinary skill in the art. Other methods and materials similar or equivalent to those described herein can be used in the practice or testing of the present invention.

EXAMPLES

Preparation of 2',7,N-tri(t-BOC)tazol (7).

Taxol (25 mg, 0.0293 mole) and acetonitrile (1.5 ml, freshly dried and distilled over calcium hydride) were added to a flame dried 25 ml round bottom flask, under argon atmosphere. To this solution was added 84.9 mg (0.389 mmole) of di-tert-butyl dicarbonate in 1.00 ml of dry acetonitrile under argon. After stirring for 5 min., DMAP (4.8 mg) was added. The reaction mixture, which became pale yellow to orange in color, was then stirred for five days; on the second and fourth days after initiating the reaction, 85 mg of di-tert-butyl dicarbonate in 0.5 ml of dry acetonitrile was added, followed by addition of 4.8 mg of DMAP. The reaction mixture was quenched by diluting it with ethyl acetate, followed by removal of the solvent on a rotary evaporator. The orange residue was then dissolved in ethyl acetate and washed with dilute HCl followed by a rapid wash with cold 0.05 N NaHCO$_3$ solution. The solution was washed with brine, dried with sodium sulfate, and the solvent was removed by use of a rotary evaporator. Purification by preparative thin layer chromatography (PTLC) (Analtech, 500 mm SiO$_2$) gave two major bands with R$_f$ 0.27 and 0.23. The band with R$_f$ 0.27 was scraped off and eluted with acetone to give the title compound on evaporation (11.1 mg, 33%) mp 188–192° C. Elution of the band at R$_f$ 0.30 gave 2',7-di(BOC) taxol (10.1 mg, 33%). For $^1$H-NMR, see Table 2; Mass Spectrometer, MS, gave m/z of 1053 (MH+).

Conversion of 2',7,N-tri-(t-BOC)-2-Debenzoyl tazol (9) to 2',7,N-tri-(t-BOC) tazol (7).

2',7,N-tri-(t-BOC)-2-debenzoyltaxol 9 (7 mg, 0.007 mmol), benzoic acid (24 mg, 0.198 mmol) and dicyclohexylcarbodiimide, DCC, (41 mg, 0.198 mmol) in 50 ml dry toluene were mixed under an argon atmosphere, and 4-pyrrolidinopyridine was added as a catalyst. The reaction mixture was stirred at room temperature (24° C.) overnight and then diluted with ethyl acetate. The residue was filtered and the filtrate was then purified by PTLC (Analtech 500 μm; hexane: ethyl acetate 1:1) to give 2',7,N-tri-(t-BOC)-taxol 7 (4.5 mg, 58%).

Preparation of 2',7,N-tri(t-BOC)-2-debenzoyltaxol 9.

To a stirred solution of 2',7,N-tri(t-BOC)taxol (34.5 mg, 0.034 mmole) in 2.5 ml of tetrahydrofuran (THF), 0.4 ml 0.1 N lithium hydroxide solution at 0° C. was slowly added. After complete addition (about 5 minutes) the ice bath was removed and the reaction mixture was stirred for 1.5 hour at room temperature. TLC showed conversion of the starting material to two new products (R$_f$ 0.28 and 0.19 in hexane:ethyl acetate, 1:1), together with unreacted starting material. The reaction mixture was then diluted with 10 ml diethyl ether, washed with brine, and dried over sodium sulfate. The solvent was evaporated on a rotary evaporator to obtain crude product, which was purified by preparative TLC (Analtech, 500 μm, SiO$_2$, hexane:ethyl acetate, 1:1) to yield 2',7,N-tri(t-BOC)2-debenzoyl taxol (R$_f$ 0.19) (8.7 mg, 24.2%). For $^1$H-NMR data, see Table 2.

Conversion of 2',7,N-tri-(t-BOC) taxol 7 to Tazol

To a solution of 50% formic acid in dry methylene chloride (200 μl 99% formic acid+200 μl dry CH$_2$Cl$_2$), 2',7,N-tri-(t-BOC) taxol (10 mg) was added and stirred for 5 hours at room temperature. The excess formic acid was removed by evaporation on a vacuum pump, and the reaction mixture was diluted with ethyl acetate, then washed with 5% NaHCO$_3$, water and brine, dried, and evaporated. Purification of the crude material by PTLC (Analtech 500 mm; hexane:ethyl acetate 1:1) yielded taxol (3 mg, 38.5%), identical with an authentic sample.

Preparation of 2',7,N-tri(t-BOC)-2-debenzoyl isotaxol 10.

If the preparation of compound 9 described above is allowed to proceed for a longer time, the spot with R$_f$ 0.28 becomes the major product. After a 3 hour reaction, 4.2 mg of this material could be isolated from 10.5 mg of starting material (56.7%). Characterization gave a melting point, Mp, of 158–160° C.; for proton NMR data, see Table 2.

Preparation of 2-Debenzoylisotaxol 11.

A mixture of 2',7,N-tri-(t-BOC)-2-debenzoyl isotaxol 10 (14 mg, 0.0133 mm), and 0.5 ml of 99% formic acid was stirred at room temperature in a 5 ml round bottom flask for 90 minutes under argon. The excess formic acid was removed under reduced pressure. The residue was diluted with ethyl acetate (10 ml), washed quickly with 0.05 N aqueous NaHCO$_3$ and brine, dried with anhydrous sodium sulfate, and evaporated. The crude product was purified by PTLC (hexane:ethyl acetate, 1:1). The lower band of R$_{f\,0.1}$ was scraped and eluted several times with acetone. Removal of the solvent gave 2-debenzoyl isotaxol 11, 3.8 mg (34%). For $^1$H-NMR data, see Table 2. MS gave m/z 772 (MNa+), 750 (MH+).

Preparation of 2'-(t-BOC)taxol 14.

Taxol (85.3 mg, 0.1 mmol) and acetonitrile (2 ml, freshly dried and distilled over calcium hydride) were added to a flame dried 25 ml round bottom flask under argon. To this solution at 0° C. was added 21.8 mg (0.1 mmol) of di-tert-butyldicarbonate in 2.00 ml of dry acetonitrile under argon. After stirring for 5 minutes, DMAP (5 mg) was added at 0° C. The reaction mixture was stirred for 2 hours at room temperature, and then worked up by diluting with ethyl acetate, followed by removing the solvent on a rotary evaporator. The pale yellow residue was then dissolved in ethyl acetate, and washed with dilute HCl, followed by a rapid wash with cold 0.05 N NaHCO$_3$. The organic solution was then washed with brine, dried over sodium sulfate, and evaporated to give 14 (95 mg, 99.6%), R$_f$ (hexane:ethyl acetate, 1:1) 0.36. For $^1$H-NMR data, see Table 3.

Preparation of 2'-(t-BOC)-7-(triethylsilyl) tazol 15.

To a stirred solution of 2'-(t-BOC)taxol (95.3 mg, 0.1 mmol) in 2 ml dry DMF, imidazole (34 mg, 5 mmol) was slowly added, followed by addition of triethylsilyl chloride (83.9 ml, 0.5 mmol) at 0° C. under argon. The reaction mixture was stirred for 3 hours at room temperature, and then quenched by diluting with ethyl acetate and washing the organic layer several times with water and brine, followed by drying with sodium sulfate. The solvent was then evaporated to obtain the pure compound 15, (94.9 mg, 89%), $R_f$ (hexane:ethyl acetate, 1:1) 0.66. For $^1$H-NMR, see Table 3.

Preparation of 2',N-di(t-BOC)-7-(triethylsilyl)taxol 16.

To a solution of 2'-(t-BOC)-7-(triethylsilyl) taxol (92.5 mg, 0.09 mmol) in 0.5 ml dry acetonitrile under argon atmosphere di-t-butyldicarbonate (377.6 mg, 20 mmol) in 0.5 ml of $CH_3CN$ was added. After stirring for 5 minutes at room temperature, DMAP (8 mg) was added. The reaction mixture was then stirred for 3 hours at room temperature, and then worked up by diluting with ethyl acetate, followed by removal of the solvent on a rotary evaporator. The residue was then diluted with ethyl acetate and washed with cold dilute HCl, cold 0.05 N $NaHCO_3$, water, and brine, and dried over sodium sulfate. The solvent was then evaporated to yield crude product, which was purified by passing through a small silica gel column to yield the pure compound 16 (89 mg, 88%). $R_f$ (hexane:ethyl acetate, 1:1) 0.55. For $^1$H-NMR data, see Table 3.

Preparation of 2',N-di(t-BOC)-7-(triethylsilyl)-2-debenzoyl tazol 17.

To a stirred solution of 2',N-(di-t-BOC)-7-(triethylsilyl) taxol (45 mg, 0.038 mmol) in 4.5 ml of THF, 0.4 5 ml of 0.1 N LiOH solution was added. The mixture was held at 0° C. with an ice bath during combination of the ingredients. After complete addition, the ice bath was removed and the solution was stirred for 2 hours at room temperature. TLC showed the presence of two new spots at lower $R_f$ along with starting material. The reaction was then worked up by diluting with ether and washing with brine. The brine layer was washed with fresh ether and the combined organic layer was dried over sodium sulfate and evaporated. The crude product was then purified on PTLC.(Analtech, 500 μm, Hexane:EtOAc, 1:1). The slower moving band was scraped and extracted to give the debenzoyl product 17 (15.3 mg, 38%). The band corresponding to starting material was also recovered (23.3 mg). $R_f$ (hexane:ethyl acetate, 2:1) 0.21. For $^1$H-NMR data, see Table 3. MS gave m/z 1064 (MH+, 100%).

Preparation of 2',N-di(t-BOC)-7-(triethylsilyl)taxol 16 From 2',N-di (t-BOC)-7-(triethylsilyl)-2-debenzoyl tazol 17.

A sample of 2',N-di(t-BOC)-7-(triethylsilyl)-2-debenzoyl taxol (2 mg, 0.0018 mole) was treated with benzoic acid (4.59 mg, 0.0338 mole), DCC (7.75 mg, 0.038 mole), and a catalytic amount of 4-pyrrolidinopyridine in dry toluene (10 μL) under argon atmosphere. The mixture was stirred overnight at 50° C., and the solvent was then removed on a rotary evaporator. The crude reaction mixture was purified by PTLC (500 mM layer, EtOAc:hexane, 1:2) to yield 2',N-di (t-BOC)-7-(triethylsilyl) taxol 16 (1.5 mg, 68%), identical with material prepared directly from taxol.

Conversion of 2',N-di(t-BOC)-7-(triethylsilyl)taxol 16 to Tazol.

Compound 16 (9.5 mg) was treated with 99% formic acid (Fluka, 0.15 ml) with stirring for 30 minutes at room temperature. The formic acid was then removed by use of a vacuum pump, and the reaction mixture diluted with ethyl acetate, washed with 5% $NaHCO_3$, water, and brine, dried and evaporated. Purification of the residue by PTLC (EtOAc:hexanes, 1:1) yielded taxol (2 mg, 28%), identical with an authentic sample.

Preparation of 2',N-di (t-BOC) -7- (triethylsilyl)-2-debenzoyl-2(3-(3-(trifluoromethyl)-3H-diazirin-3-yl) phenoxyacetyltaxol.

2',N-di(t-BOC-7-triethylsilyl-2-debenzoyltaxol (17) (2.34 Mg, 0.002 Mmol), 3-(3-(trifluoromethyl)-3H-diazirin-3-yl) phenoxyacetic acid (10.4 mg, 20 mmol) and DCC (8.25 mg, 20 mmol) in 50 μl of dry toluene were mixed at room temperature under argon and 4-pyrollidinopyridine was added as a catalyst. The reaction mixture was stirred at room temperature overnight and then diluted with ethyl acetate. The residue was filtered and the filtrate was purified by PTLC (Analtech, 500 μm:hexane:EtOAc, 1:1) to give 1.1 mg of the title compound (38.3%). $^1$H-NMR, see Table 4.

Preparation of 2',7-Di(triethylsilyl)-2-debenzoyl tazol 22.

To a stirred solution of 2',7-di(triethylsilyl) taxol 21, (65.0 mg, 0.060 mmol) prepared according to the procedure described in "Modified Taxols. 5. Reaction of Taxol With Electrophilic Reagents and Preparation of a Rearranged Taxol Derivative with Tubulin Assembly Activity," *J. Org. Chem.*, 56, 5114–5119 (1991). Benzene:methylene chloride (8:1.2 ml) and tetrabutyl-ammonium hydrogen sulfate (500 mg) at room temperature 8 ml of aqueous 2 N sodium hydroxide solution was added. The reaction mixture was stirred for 1.5–2 hours, and then diluted with 15 ml of benzene. The organic layer was separated, washed with water (3×10 ml), brine (10 ml), dried over $MgSO_4$, and evaporated. The crude product was purified on PTLC (Analtech, 500 μm, hexane:EtOAc, 1:1). The slower moving band ($R_f$=0.3) was extracted to give the 2',7-di (triethylsilyl)-2-debenzoyl taxol 2 (25.0 mg, 43%). For $^1$H-NMR data, see Table 4. Two faster moving bands ($R_f$ 0.32 and 0.75) on extraction gave starting material 1 (25.0 mg) and 7-TES-baccatin-III (5.0 mg). Yield was 69% based on unrecovered starting material.

Acylation of 2',7-di(triethylsilyl)-2-debenzoyl taxol With m-nitro-benzoic Acid

A mixture of 2',7-di (triethylsilyl) -2-debenzoyl taxol 22 (10.0 mg, 0.01 mmol), DCC (42.0 mg, 0.20 mmol), 4-pyrrolidinopyridine (catalytic quantity), p-nitrobenzoic acid (0.20 mmol), and toluene (0.1 mL) was stirred at room temperature for 12 hours and then diluted with (10 ml) of ethyl acetate, EtOAc. The organic layer was separated and washed with water (2×5 ml), brine (2×5 ml), dried over $MgSO_4$ and evaporated. The crude product was purified on PTLC (Analtech, 500 μm, hexane:EtOAc, 1:1). The band ($R_f$ 0.72) was extracted to furnish 2-debenzoyl-2- (m-nitro benzoyl)-2', 7-di (triethylsilyl) taxol 23c (yield 60 to 75%). For $^1$H-NMR, see Table 4.

Deprotection of 2-debenzoyl-2-(m-nitrobenzoyl)-2',7-di (triethylsilyl) Taxol

A mixture of 2-debenzoyl-2-(m-nitrobenzoyl)-2', 7-di (triethylsilyl) taxol 23c (10.0 mg) and (0.10 mL) of 5% HCl:MeOH was stirred at room temperature for 0.5 hours and then diluted with (10 mL) of EtOAc. The organic layer was separated and washed with water (2×5 mL), brine (5 mL), dried over $MgSO_4$ and evaporated. The crude product was purified on PTLC (Analtech, 500 μm, hexane:EtOAc, 1:1). The band ($R_f$ 0.2) was extracted to give 2-debenzoyl-2-(p-nitrobenzoyl) taxol derivative 13c (yield 80 to 90%). For $^1$H-NMR, see Table 2.

Preparation of 2-(m-Azidobenzoyl)-2-debenzoyl-2',7-di (triethylsilyl) Tazol 23f.

To a solution of 2-debenzoyl-2',7'di (triethylsilyl) taxol 22, (21 mg, 0.002 mmol) in dry toluene (200 μl), 1,3-dicyclohexylcarbodiimide (88 mg, 0.043 mmol), m-azidobenzoic acid (70 mg, 0.043 mmol), and a catalytic amount of 4-pyrrolidinopyridine were added, and stirred at 50° C. for 3 hours. The crude reaction mixture was filtered through a short silica gel column using 20% ethyl acetate/80% hexane. The required product along with some inseparable impurities co-eluted, and hence the crude product (25 mg) was carried through the next reaction. For $^1$H-NMR data, see Table 5.

Preparation of 2-(m-Azidobenzoyl)-2-debenzoyl Tazol 13f.

To crude 2-(m-azidobenzoyl)-2-debenzoyl-2',7-di (triethylsilyl) taxol (22.1 mg), 200 μl of freshly prepared 5% HCl in methanol was added. The reaction mixture was stirred at room temperature for 30 minutes, and then diluted with 20 ml of ethyl acetate. The organic layer was washed with water (10 ml×30) and brine and dried over sodium sulfate. The crude product was purified by PTLC (500 μM layer, hexane:ethyl acetate, 1:1) to yield 2-(m-azidobenzoyl)-2-debenzoyl taxol 13f (16 mg, 83%). For $^1$H-NMR data, see Table 5.

In a preferred embodiment, compounds of the present invention having antineoplastic properties are administered in antineoplastic amounts to patients suffering from cancer. for example, 2-debenzoyl-2-meta-azido-benzoyl taxol can be administered in a pharmaceutically acceptable carrier in an antineoplastically effective amount to a patient suffering from cancer. Likewise, water soluble derivatives may be made of the antineoplastically effective compounds of the present invention and administered in an effective amount to cancer patients. Thus, the present invention discloses methods for selective deacylation and reacylation of the C-2 position on taxol and taxol analogues, as well as new antineoplastically effective compounds which result therefrom.

The compounds and methods of the present invention are not limited to the specific examples discussed in the section entitled Detailed Description of the Invention. The methods of the present invention are broadly applicable and can be used to prepare a large variety of taxol and baccatin III analogues in which the tetracyclic taxane nucleus is acylated at the C-2 position. A wide array of taxol and baccatin III analogues may be used as starting materials in the methods of the present invention. This invention further contemplates reactions, such as acylations, prior to and subsequent to acylation of the C-2 position which can produce a wide variety of compounds. Various synthetic steps such as protecting steps (for example at the C-2' and C-7 positions), and acylating and deacylating steps (for example at the C-10 and C-13 positions) may be those described herein or those otherwise known in the prior art. The products of the present invention may be prepared as either desired final products, or as intermediates in the synthesis of desired taxol analogues.

It is contemplated that substituents on the tetracyclic taxane nucleus be selected based upon the medicinal or synthetic characteristics that various substituents will impart to the taxol analogue. Workers of ordinary skill in the chemical and pharmaceutical arts will appreciate that the widely applicable methods of the present invention enable the strategic selection of substituents (from a very large number of possible substituents which could be placed on the tetracyclic taxane nucleus) at certain locations on the taxane tetracyclic nucleus.

Although preferred embodiments have been described herein, it is to be understood that the invention can be practiced otherwise than as specifically described.

TABLE I

CYTOTOXICITY OF SELECTED
2-DEBENZOYL-2-ACYLTAXOLS AGAINST P-388 LEUKEMIA

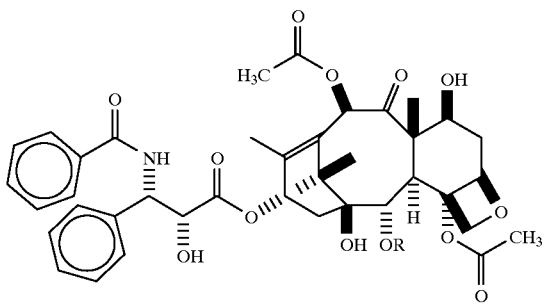

| COMPOUND | R | $ED_{50}/ED_{50}$ (taxol) |
|---|---|---|
| 1 (Taxol) | benzoyl | 1.0 |
| 13a | m-aminobenzoyl | 1500 |
| 13b | cinnamoyl | 10 |
| 13c | m-nitrobenzoyl | 0.3 |
| 13d | m-chlorobenzoyl | 0.1 |
| 13e | m-dinitrobenzoyl | 2.0 |
| 13f | m-azidobenzoyl | 0.002 |
| 13g | 3,4,5,-trimethoxy benzoyl | 0.5 |
| 13h | m-cyano | 0.25 |
| 13i | m-trifluoro methylbenzoyl | 15 |
| 13j | m-fluorobenzoyl | 0.35 |
| 13k | 2-thiophene-carbonyl | 10 |
| 13l | 2-thiophene-carbonyl | 4 |
| 13m | 3,4-dichlorobenzoyl | 0.003 |
| 13n | m-methylbenzoyl | 0.04 |

TABLE I-continued

CYTOTOXICITY OF SELECTED 2-DEBENZOYL-2-ACYLTAXOLS AGAINST P-388 LEUKEMIA

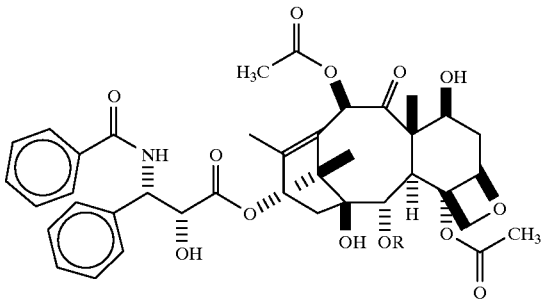

5

| COMPOUND | R | $ED_{50}/ED_{50}$ (taxol) |
|---|---|---|
| 13o | o-chlorobenzoyl | 0.011 |
| 13p | m-methoxybenzoyl | 0.0004 |
| 13q | m-chlorobenzoyl | 0.0014 |
| 13r | m-phenoxybenzoyl | 4.3 |
| 13s | m-iodobenzoyl | 0.028 |
| 13t | 3,5-difluorobenzoyl | 0.00004 |
| 13u | 2-naphthoyl | 10 |
| 13v | 3-furoyl | 1.4 |
| 13w | acetyl | 28 |
| 13x | phenoxyacetyl | 0.7 |
| 13y | p-fluorobenzoyl | 0.5 |
| 13z | p-(t-BOC)benzoyl | 30 |
| 13aa | p-cyanobenzoyl | 30 |
| 13bb | p-chlorobenzoyl | 150 |
| 13cc | p-(methylthio) benzoyl | 12 |
| 13dd | p-nitrobenzoyl | 8.3 |
| 13ee | p-trifluoro methylbenzoyl | 30 |
| 13ff | p-acetylbenzoyl | 30 |

TABLE 2

$^1$H-NMR Spectra of Compounds 6, 7, 9, 10

| protons | 2',7-di(t-BOC) taxol (6) | 2',N-tri(t-BOC) 2-debenzoyl isotaxol (10) | 2',7,N-tri(t-BOC) 2-debenzoyl isotaxol (10) | 2',7,N-tri(t-BOC) taxol (7) | 2-Debenzoyl isotaxol (11) |
|---|---|---|---|---|---|
| C-2 | 5.75 d (7.0) | 4.06 bd (6.5) | 4.06 bd (6.5) | 5.6 d (7.0) | 4.17 brd (3.2) |
| C-3 | 3.95 brd (7.0) | 3.36 bd (6.5) | 3.36 bd (6.5) | 3.9 d (7.0) | 3.25 bd (6.2) |
| C-5 | 4.95 bd (10) | 4.78 dd (9.0, 2.0) | 4.78 dd (9.0, 2.0) | 4.95 dd (7.7, 2.0) | 3.78 m |
| C-6 | — | — | — | 2.65 m | — |
| C-7 | 5.35 m | 4.33 m | 4.33 m | 5.35 dd (10.4, 3.5) | 4.3 dd (10.0, 4.0) |
| C-10 | 6.52 s | 6.59 s | 6.59 s | 6.47 s | 6.20 s |
| C-13 | 6.24 bt (8.5) | 5.96 m | 5.96 m | 5.97 m | 6.28 dt (9.0, 2.0) |
| C-16 Me | 1.2 s | 1.14 s | 1.14 s | 1.06 s | 1.09 s |
| C-17 Me | 1.25 s | 1.26 s | 1.26 s | 1.12 s | 1.25 s |
| C-18 Me | 2.1 d (1.5) | 1.86 (1.5) | 1.86 (1.5) | 1.86 d (1.5 | 1.76 bs |
| C-19 Me | 1.8 s | 1.34 s | 1.34 s | 1.75 s | 1.61 s |
| C-20 | 4.2 d (8.5) | 4.37 d (11.5) | 4.37 d (11.5) | 4.38 d (8.3) | 4.38 d (11.5) |
|  | 4.35 d (8.5) | 3.64 d (11.5) | 3.64 d (11.5) | 4.12 d (8.3) | 3.7 d (11.5) |
| C-2' | 5.4 d (3.0) | 5.94 d (11.2) | 5.94 d (11.2) | 5.94 d (11.2) | 4.67 dd (5.5, 2.0) |
| C-3' | 5.95 dd (9.0, | 5.87 d (11.2) | 5.87 d | 5.87 d | 5.7 d |
| 3' NH | 6.96 d (9.0) | — | — | — | 6.87 d (8.8) |
| O Bz (o) | 8.13 dd (8.5, 1.5) | — | — | 8.08 d (7.0) | — |
| O Bz (m + p) N-Bz 3'-Ph | 7.76 dd (8.0, 1.5) (N-Bz), 7.35–7.65 (m) O-Bz(m + p), N-Bz (m + p), | N-Bz 3'Ph = 7.33–7.63 (m) | N-Bz 3'Ph = 7.33–7.63 (m) | 7.15–7.7 (m) | 7.37–7.54 m |

TABLE 2-continued $^1$H-NMR Spectra of Compounds 6, 7, 9, 10

| protons | 2',7-di(t-BOC) taxol (6) | 2',N-tri(t-BOC) 2-debenzoyl isotaxol (10) | 2',7,N-tri(t-BOC) 2-debenzoyl isotaxol (10) | 2',7,N-tri(t-BOC) taxol (7) | 2-Debenzoyl isotaxol (11) |
|---|---|---|---|---|---|
| 4-OAc | 3'Ph 2.45 s | 2.10 s | 2.10 s | 2.4 s | 2.38 s |
| 10-OAc | 2.15 s | 2.3 s | 2.3 s | 2.18 s | 2.23 s |
| OCOC(CH$_2$)3 | 1.45 bs | 1.41 s | 1.41 s | 1.45 s | |
|  |  | 1.37 s | 1.37 s | 1.36 s | |
|  |  |  |  | 1.27 s | |
| 2' OH | — | — | — | — | 3.46 d (5.5) |

TABLE 3

$^1$H-NMR Spectra of Compounds 14, 15, 16, 17

| protons | 2'-(t-BOC) taxol (14) | 2'-(t-BOC)-7-TEStaxol (15) | 2',N-di(t-BOC)-7-TEStaxol (16) | 2',N(di(t-BOC)-7-TES-2-debenzoyl taxol (17) |
|---|---|---|---|---|
| C-2 | 5.7 d (7.0) | 5.7 d (7.0) | 5.6 d (7.0) | 3.86 bt (3.9) |
| C-3 | 3.8 d (7.0) | 3.84 d (7.0) | 3.74 d (7.0) | 3.37 d (6.8) |
| C-5 | 4.97 d (7.5) | 4.94 d (8.39) | 4.93 d (7.8) | 4.95 d (10.37) |
| C-7 | 4.45 dd ( ) | 4.49 dd (6.58, 3.8) | 4.46 dd (6.64, 3.79) | 4.4 dd (6.4, 3.7) |
| C-10 | 6.3 s | 6.46 s | 6.5 s | 6.32 s |
| -13 | 6.28 t (5.9) | 6.25 t (8.2) | 5.97 m | 6.0 m |
| -16 Me | 1.13 s | 1.18 s | 1.18 s | 1.18 s |
| C-17 Me | 1.21 s | 1.22 s | 1.2 s | 1.25 s |
| C-18 Me | 1.9 s | 2.04 s | 2.18 s | 2.15 s |
| C-19 Me | 1.68 s s | 1.69 s | 1.61 s | 1.65 s |
| C-20 | 4.32 d (8.4) | 4.32 d (8.4) | 4.27 d (8.32) | 4.58 bs |
|  | 4.2 d (8.4) | 4.18 d (8.4) | 4.06 d (8.32) | |
| C-2' | 5.4 d (2.8) | 5.4 d (2.8) | 5.99 d (11.2) | 6.08 d (10.9) |
| C-3' | 5.97 d (2.8) | 5.99 d (2.8) | 5.86 d (11.2) | 5.95 d (10.9) |
|  | 5.93 d (2.8) | 5.95 d (2.8) |  |  |
| 3' NH | 6.96 d (9.26) | 6.95 d (9.25) | — | — |
| O-Bz (O) | 8.15 d (7.3) | 8.14 d (7.3) | — | — |
| O-Bz (m + P) | 7.3–7.8 m | 7.3–7.7 m | 7.1–7.8 m | 7.25–7.8 m |
| N-Bz |  |  |  |  |
| 3'Ph |  |  |  |  |
| 4-OAc | 2.5 s | 2.45 s | 2.38 s | 2.3 s |
| 10-OAc | 2.22 s | 2.16 s | 2.16 s | 2.16 s |
| OCOC(Me)3 | 1.45 s | 1.47 s | 1.48 s | 1.48 s |
|  |  |  | 1.4 s | 1.3 s |
| SiCH2CH3 |  | 0.59 q | 0.59 q | 0.59 q |
|  |  | 0.92 t | 0.92 t | 0.92 t |
| Other |  |  |  |  |

$^a$Aromatic protons of diazirine ring
$^b$ArOCH$_2$COOR

TABLE 4

$^1$H-NMR Spectra of Compounds 22 and 13c

| protons | 2',7-DiTES-2-debenzoyltaxol (22) | 2-Debenzoyl-2-m-NO$_2$-benzoyl-taxol (13c) | 2',N-di(t-BOC)-7-triethylsilyl)-2-debenzoyl-2-(3-(3-trifluoromethyl)-3H-diazirin-3-yl)-phenoxyacetyltaxol |
|---|---|---|---|
| C-2 | 3.93 t (6.3) | 5.66 d (7.2) | 5.45 d (7.1) |
| C-3 | 3.47 d (6.8) | 3.86 d (7.2) | 3.67 d (7.1) |
| C-5 | 4.95 d (9.5) | 4.98 d (8.1) | 4.95 d (8.2) |
| C-6 | 2.5 m | 2.5 m | 2.55 m |
| C-7 | 4.41 dd (6.63, 10.52) | 4.42 m | 4.45 m |
| C-10 | 6.36 s | 6.29 s | 6.4 s |
| C-13 | 6.21 t (9.7) | 6.20 t (8.7) | 6.0 s |
| C-16 Me | 1.06 s | 1.15 s | 1.10 s |
| C-17 Me | 1.13 s | 1.26 s | 1.26 s |
| C-18 Me | 2.03 s | 1.83 s | 1.78 s |
| C-19 Me | 1.6 s | 1.68 s | 1.60 s |
| C-20 | 4.6 m | 4.7 dd (7.9, 4.4) | 4.47 d (7.6) |
|  |  |  | 4.2 d (7.6) |
| C-2' | 4.6 m | 4.84 dd | 6.03 d (10.9) |
| C-3' | 5.66 d (9.4) | 5.75 dd (1.5, 8.8) | 5.92 d (10.9) |
| 3'-NH | 7.1 d (9.4) | 6.85 d (8.8) | — |
| O-Bz(O) | — | — | — |
| O-Bz (m + p) | 7.3–7.9 m | 7.3–7.95 m | 7.3–7.66 m |
| N-Bz |  |  |  |
| 3'-Ph |  |  |  |
| 4-OAc | 2.38 s | 2.42 s | 2.25 s |
| 10-OAc | 2.13 s | 2.25 s | 2.12 s |
| SiCH$_2$CH$_3$ | 0.59 q | 0.59 q | 0.6 q |
|  | 0.92 t | 0.92 t | 0.9 t |
| Other | 3.1$^a$ d (5.27) | 8.44 m, 9.07 bbs | 6.69 bs$^a$, 6.90 dd$^a$, 6.98 dd$^a$ 4.6 d$^b$ |

$^a$2'-hydroxy
$^b$2"- and 4"-positions of the m-nitrobenzoyl ring.

TABLE 5

$^1$H-NMR Spectra of Compounds 23f and 13f

| Protons | 2(m-azidobenzoly-2-debenzoyl-2',7-di(triethylsilyl taxol (23f) | 2-(m-azidobenzoyl)-2-debenzoyltaxol (13f) |
|---|---|---|
| C-2 | 5.67 d* | 5.67 d (7.0) |
| C-3 | 3.65 d (7.2) | 3.81 d (7.0) |
| C-5 | 4.95 d (9.1) | 4.95 dd (7.7, 0.83) |
| C-6 | 2.50 m | 2.55 m |
| C-7 | 4.48 m | 4.41 m |
| C-10 | 6.49 s | 6.27 s |
| C-13 | 6.21 bt* | 6.21 bt (7.9) |
| C-16 Me | — | 1.14 s |
| C-17 Me |  | 1.24 s |

TABLE 5-continued

¹H-NMR Spectra of Compounds 23f and 13f

| Protons | 2(m-azidobenzoly-2-debenzoyl-2',7-di(triethylsilyl taxol (23f) | 2-(m-azidobenzoyl)-2-debenzoyltaxol (13f) |
|---|---|---|
| C-18 Me | | 1.80 s |
| C-19 Me | | 1.68 s |
| C-20 | 4.38 d (8.1) | 4.33 d (7.79) |
|  | 4.20 d (8.1) | 4.118 d (8.26) |
| C-2' | 4.70 s | 4.77 bs |
| C-3' | 5.72 d* | 5.75 dd (8.84, 2.21) |
| 3'-NH | — | 6.95 d (8.87) |
| O-Bz (O) | — | — |
| O-Bz (m + p) | 7.10–7.55 m | 7.20–7.55 m |
| N-Bz | | |
| 3'-Ph | | |
| 4-OAc | 2.55 s | 2.36 s |
| 10-OAc | 2.20 s | 2.23 s |
| SiCH₂CH₃ | 0.50 t, 0.70 q | |
|  | 0.85 t, 1.00 q | |
| Other | 7.70–7.95ᵃ | 7.70–7.95ᵃ m |

*NMR signals are overlapped with impurity.
ᵃAromatic protons of m-azidobenzoyl group.

We claim:

1. Taxol modified to possess a hydroxy group at the C-2 position of the B ring of the tetracyclic taxane nucleus.

* * * * *